United States Patent
Bons et al.

(10) Patent No.: US 10,132,759 B2
(45) Date of Patent: Nov. 20, 2018

(54) FISSURE-DETECTION AGENT, METHOD FOR THE PRODUCTION THEREOF AND USE OF THE FISSURE-DETECTION AGENT

(71) Applicant: Chemetall GmbH, Frankfurt am Main (DE)

(72) Inventors: Peter Bons, Reichelsheim (DE); Rüdiger Rein, Bad Vilbel (DE); Jörg Wörner, Bruchköbel (DE); Finlay Aiston, Frankfurt (DE)

(73) Assignee: Chemetall GmbH, Frankfurt am Main (DE)

( * ) Notice: Subject to any disclaimer, the term of this patent is extended or adjusted under 35 U.S.C. 154(b) by 389 days.

(21) Appl. No.: 15/028,124

(22) PCT Filed: Oct. 7, 2014

(86) PCT No.: PCT/EP2014/071407
§ 371 (c)(1),
(2) Date: Apr. 8, 2016

(87) PCT Pub. No.: WO2015/052164
PCT Pub. Date: Apr. 16, 2015

(65) Prior Publication Data
US 2016/0252462 A1 Sep. 1, 2016

(30) Foreign Application Priority Data

Oct. 9, 2013 (DE) .................. 10 2013 016 674

(51) Int. Cl.
*C09K 11/06* (2006.01)
*G01N 21/91* (2006.01)
*C09B 67/22* (2006.01)
*C09B 67/42* (2006.01)
*G01M 3/22* (2006.01)

(52) U.S. Cl.
CPC ......... *G01N 21/91* (2013.01); *C09B 67/0033* (2013.01); *C09B 67/0071* (2013.01); *G01M 3/22* (2013.01)

(58) Field of Classification Search
CPC .............. C09B 67/0033; C09B 29/065; C09B 29/0955; C09B 69/08; C09B 67/0071; C09B 67/0086; G01M 3/22; G01N 21/91; Y10S 252/96; C09K 11/06
See application file for complete search history.

(56) References Cited

U.S. PATENT DOCUMENTS

| | | |
|---|---|---|
| 2,953,530 A | 9/1960 | Switzer |
| 3,981,185 A | 9/1976 | Molina |
| 2010/0021701 A1 | 1/2010 | Heinrichs |

FOREIGN PATENT DOCUMENTS

WO 2007/133563 A1 11/2007

*Primary Examiner* — Stella K Yi
(74) *Attorney, Agent, or Firm* — Armstrong Teasdale LLP

(57) ABSTRACT

The invention relates to fissure-detection agents for fault detection according to the penetration method of metallic and/or non-metallic components, which are a microemulsion comprising at least 10 wt. % of water A), at least 0.1 wt. % of at least one dye B), at least 5 wt. % of at least one substantially water-insoluble liquid phase C) and at least 2 wt. % of at least one surfactant D) selected from non-ionic, anionic and/or amphoteric surfactants, the sum of all constituents being 100 wt. %, wherein the fissure-detection agent has a mean particle size in the range of 1 to 250 nm and a transparency of at least 70% at 600 nm. The invention also relates to the production of said fissure-detection agents, to a process for their preparation or/and disposal, and their use.

15 Claims, No Drawings

FISSURE-DETECTION AGENT, METHOD FOR THE PRODUCTION THEREOF AND USE OF THE FISSURE-DETECTION AGENT

REFERENCE TO RELATED APPLICATIONS

This is a National Stage entry of International Patent Application PCT/EP2014/071407, filed on Oct. 7, 2014, which application claims priority from German Application No. 102013016674.8, filed Oct. 9, 2013. Each patent application identified above is incorporated herein by reference in its entirety.

The invention relates to penetrant testing media in the form of microemulsions with low average particle size and with high transparency, to methods for producing water-based penetrant testing medium microemulsions and to methods for their preparation, in which at least one dye is dissolved in an organic solvent, as well as the use of the penetrant test media for testing and fault detection according to the penetrant testing method, in particular for metallic workpieces. However, the penetrant testing media according to the invention are not aqueous or oil-based and/or surfactant-based solutions. Rather, they are microemulsions, in contrast to the penetrant testing media of the prior art, and have a more environmentally friendly composition in comparison to the same. Testing media are used for example in the aerospace industry, in the automotive industry, in apparatus and mechanical engineering, and in the so-called general industry. Penetrant testing media are used for detecting defects such as fine pores and/or fine cracks. In particular, they are used for detecting defects that are open toward the surface, and that have a diameter of $\geq 10$ µm, or possibly even $\geq 1$ µm diameter and/or a gap width of $\geq 10$ µm or possibly even $\geq 1$ µm. The errors are made detectable to the human eye by the addition of at least one dye. Often the dye is incorporated into a dye system, so that the term "dye system" within the meaning of the present application indicates at least one dye, and optionally all additives which are useful for optimizing detectability, for stable integration of the dye and/or for dissolving the dye, such as brighteners, for example. Within the context of this application, substantially non-water-soluble solvents which fall in the category of compounds in substantially non-water-soluble phases, and the surfactants D) used for the same, selected from among anionic surfactants a), nonionic surfactants b), and/or amphoteric surfactants c) are included under the rubric of substances C) and/or D) respectively. In the prior art, penetrant testing media are also distinguished by their color differentiation: fluorescence testing and/or color contrast testing—for example, red-white contrast.

Penetrant testing media are divided into defect detectability levels in AMS 2644 and ISO 3452, particularly in parts 2 and 3. The yellow fluorescent penetrant testing media according to the invention are divided in this case into levels 0.5, 1, 2, 3, and 4—the penetrant testing medium for red-white testing as well as the red fluorescent penetrant testing media in levels 1 and 2, wherein the levels 4 and/or 2 clarify the highest test sensitivity.

The penetrant testing media of the prior art are a) aqueous solutions with at least one surfactant, which often also have a content or even high content of organic solvent, or b) waterless solutions based on organic solvent, disregarding any absorption of moisture from the air and/or from impurities, or c) oil-based solutions, or d) waterless solutions based on surfactants. The solubility of the dye or dye system used is determined, for the aqueous solutions a), by the content and the type of surfactant, by the content of water and by the addition of water-soluble solvents—typically water-soluble glycols and/or water-soluble glycol ethers.

The penetrant testing media of the prior art exhibit at least one of the following disadvantages:

1) They are either aqueous solutions not containing a substantially water insoluble solvent for the water-insoluble dye, and they have such a small amount of dye that the detectability of voids is significantly reduced due to the low content of dye. They typically contain dyes which are oil-soluble and/or soluble in organic solvents. Although these penetrant testing media are usually environmentally friendly, they have very low detection ability due to the low dye content, such that they belong under level 0.5, as yellow fluorescent penetrant testing media.

2) Or, they contain a solvent system based on water and water-soluble monohydric alcohols, polyhydric alcohols and/or glycol ethers, in which the dye is dissolved only in such a small proportion that the detectability of defects is significantly reduced due to the low solubility of the dye or the dye system. They typically contain dyes which are oil-soluble and/or soluble in organic solvents. Therefore, these penetrant testing media belong under level 0.5 or 1 as yellow fluorescent penetrant testing media, and are usually largely environmentally friendly, but also have relatively weak defect detectability.

3) Typically, the dyes used are soluble in oil and/or in organic solvents, and these dyes are not soluble in water, or the >20 g/L of water-soluble dyes are, as sulfur- or chloride-containing compounds, usually undesirable. These sulfur or halogen-containing penetrant testing media are indeed water-soluble and are clear solutions, but are usually not used because of the corrosive attack of metallic materials.

4) Or, the penetrant testing media of the prior art are oil-based and water-insoluble, or due to very high levels of predominantly environmentally unfriendly additives a) such as plasticizers, for example, often as far more than 40 wt-%, b) such as water-insoluble organic solvents, for example, based on esters and/or ethers, often as more than 40 wt %, and/or c) such as surfactants, for example, often as more than 30 wt %, are very environmentally unfriendly. They are completely free of water at delivery and are clear solutions. Here, the yellow fluorescent penetrant testing medium with the highest sensitivity, i.e., in classes 3 and 4, has the disadvantage that residues of the penetrant testing medium can settle on the surface of the test object when the excess penetrant testing medium is washed off before the end of the testing, and cannot be removed upon further rinsing with water. These residues can only be removed with an aqueous emulsifier or with an organic solvent or solvent mixture during an additional elaborate further cleaning before the visual inspection and evaluation.

DE 28 11 561 A1 discloses a water-rinsable, washing-resistant, biologically degradable penetrating dye composition containing the dye and at least 70 wt % of a primary alcohol ethoxylate.

All penetrant testing media of the prior art which can be obtained by the inventors as mixtures, or are known via their specifications, are clear solutions, and are neither emulsions nor microemulsions. They always have an average particle size measured with a Zetasizer Nano ZS, from Malvern, of under 1 nm, which is a clear indication of solutions.

Due to the low water solubility of the dyes, up to now, significant amounts of water-soluble organic solvents have needed to be added as solubilizer. The dye systems typically contain at least one organic dye, and optionally at least one brightener, which is also referred to as a color enhancer. The organic solvents reduce the viscosity, help improve penetration, in particular into cracks, and/or function as diluents in the case of oil-based penetrant testing media.

Therefore, water-based penetrant testing media according to the prior art usually contain either 5 to 70 wt % of at least one water-soluble organic solvent, and 30 to 75 wt % of water in oil-free compositions, or typically from 5 to 30 wt % of at least one organic-based and often water-insoluble solvent in oil-based, and mostly 30 to 70 wt % oil-containing and anhydrous, or nearly anhydrous, compositions. The oils in this case are usually mineral oils or derivatives thereof, optionally with an addition of at least one plasticizer.

These penetrant testing media of the prior art are significantly less environmentally friendly than those of the present application, in particular due to the lack of or low water content and/or due to the oil content being mineral oil and/or derivatives thereof, when penetrant testing media of the same detectability levels are compared. These solvents primarily function to dissolve the water-insoluble components, but also to reduce viscosity and improve penetration behavior, especially in cracks. They usually contain from 0.4 to 4 wt % of components of the dye system in oil-free compositions, and typically from 0.4 to 7 wt % in oil-based compositions, as well as 10 to 50 wt % of at least one surfactant. In this case, in many penetrant testing media, at least one surfactant also functions as the organic solvent as well, and the sum of all the constituents is 100 wt %. Low solubility of the components of the dye or the dye system in mixtures causes a very low detection sensitivity. This low detection sensitivity is found, for example, at a solubility of not more than 0.3 wt % of the components of the dye or dye system in mixtures with at least 25 wt % of surfactant in water. This low detection sensitivity is found, for example, at a solubility of not more than 0.3 wt %, of the components of the dye or dye system in mixtures with up to 50 wt % of surfactant in water.

Also, aqueous test media not containing organic solvent are very limited with respect to their detection sensitivity. They also have difficult application behavior, marked by difficulties in removing excess penetrant from the surface by rinsing with water. Inadequate rinsing of excess penetrant test media after the application and after the contact time decreases the detectability of defects as the result of reduced contrast, which may be caused by residues of the dye or dye system on the surface. Excessive rinsing can quickly lead to the penetrant being washed out of the defect. This occurs especially in the case of aqueous solutions.

By way of example, Ardrox® 920A is used in fluorescent penetrant testing as a surfactant-containing solution with a high water content. Moreover, Checkmor® 240 is offered as an anhydrous oil-containing solution for red and white testing.

Penetrant testing media of the prior art often use water-insoluble organic solvents, which are necessary for dissolving all the constituents of the dye or the dye system, and which are often anhydrous. Penetrant testing media of the prior art load the rinsing water with organic compounds that cannot be removed with a conventional wastewater treatment, because they always contain solubilizers as well which are organic water-miscible solvents based on polyhydric alcohols and their ethers. Due to the good solubility of surfactants and organic solubilizers in water, high levels of chemical oxygen demand COD and high levels of biological oxygen demand BOD result.

For this reason, there has been a need to propose penetrant testing media that overcome at least one of the above-mentioned disadvantages has existed. There has also been a need to suggest penetrant testing media with the simplest possible composition, which can be produced as simply as possible, and/or can be easily used for defect detection. Moreover, there has been a need for methods for producing these penetrant testing media. Finally, there has been a need to propose methods for the processing and/or disposal of these penetrant testing media.

However, it has now been found that it is possible to produce penetrant testing media, which have a higher water content than the penetrant testing media of the prior art at a comparatively high content of dissolved components of the dye or dye system. This also makes them more environmentally friendly. They can accommodate a higher water content than aqueous solutions if microemulsions are produced. It has now also been possible to reduce the content of solubilizers in penetrant testing media significantly, and possibly to even avoid the use thereof, wherein the same are almost always necessary in the penetrant testing media of the prior art and are harmful to the environment. The penetrant testing medium according to the invention can be used particularly successfully for defect detection, and exceed the detection ability of penetrant testing media according to the prior art many times over. They have also been found to be particularly advantageous for the disposal of penetrant testing media.

It has now also been possible to provide penetrant testing media for red-white testing and for fluorescence testing that work well with an increased proportion of water, and have a largely environmentally friendly composition. The penetrant testing media according to the invention are preferably oil-free or substantially free of oil, particularly in the case of yellow fluorescent compositions. However, quantities of oil which are not always well-marked can occur in commercial products in certain cases. Oil can also show a minor role in red dyes as solvent.

In this process, it has now also been found that it is possible and particularly advantageous to make penetrant testing media as a microemulsion because microemulsions exhibit increased cleaning power, because they often enable higher water content, and because it is often possible to add greater amounts of dye such that increased detectability levels are achieved due to the higher dye content. Despite intensive research and testing of the penetrant testing media on the market, it has not been possible to identify any penetrant testing media in the form of microemulsions.

It has now been found that it is possible and advantageous to at least partially replace the often high content of solubilizers (co-solvents), which are usually water-soluble alcohols and/or water-soluble polyols having a solubility in water at 20° C. of at least 10 g/L, with water-insoluble solvents, with substantially water-insoluble solvents, and/or surfactants, wherein the sum of the solubilizers is often at least 20 wt % less than the original amount of such solubilizers in products of the prior art. In this case, O/W microemulsions in particular, especially solvents such as substantially water-insoluble glycol ethers, are used, the same dissolved in water in the range from 0 to 60 g/L at 20° C. at atmospheric pressure, and/or in particular water-soluble nonionic and/or anionic surfactants such as alcohol ethoxylates having a water solubility at 20° C. of at least 10 g/L. Where solubility figures are given at 20° C., then for the purposes of this application atmospheric pressure is always assumed. These solvents typically have very good solubility for the dyes and/or dye systems used.

Up to now there was the risk during defect testing that cracks and other defects cannot be adequately detected with conventional water-based penetrant testing media due to insufficient cleaning of the test objects. It has now been found that penetrant testing media in the form of a microemulsion have high internal kinetic activity due to constant reconfiguration of the micelles. This effect leads to an additional cleaning power which can compensate for a potentially inadequate cleaning and/or degreasing of the parts to be tested. Therefore, the penetrant testing medium microemulsions according to the invention are excellently suited for the reliable detection of errors.

Dispersions and emulsions are in some cases very intransparent, and often even milky. Microemulsions are macroscopically homogeneous, optically transparent or clear, low and usually thermodynamically stable mixtures. They often show a viscosity of less than 30 mrvVs as measured with a capillary viscometer at 20° C. at atmospheric pressure. Emulsions, microemulsions and their segregated variants are addressed within the context of the present application, by the preamble thereof, as dispersions.

Compared to purely aqueous penetrant testing media containing highly water-soluble organic solvents, the microemulsions of the invention can dissolve a significantly higher amount of water-insoluble dye, including all components of a dye system such as dye and fluorescence amplifier In this way, a detection sensitivity is achieved with these water-containing systems that was previously achieved only for penetrant testing media of the prior art with a content of at least 50 wt % of surfactants, and potentially a content of solubilizers which dissolve the components of the dye or the dye system.

The term 'microemulsion' is typically understood to mean a thermodynamically stable, optically isotropic dispersion containing at least two immiscible liquids, liquid mixtures, or solutions, optionally stabilized by at least one amphiphilic component such as an emulsifier; a microemulsion in this case is similar to an emulsion but the disperse phase of the microemulsion, such as oil or water, forms such small domains—so-called "droplets"—that visible light is not or not significantly scattered by them. The result is that microemulsions are transparent or clear like, for example, water while other dispersions and emulsions are often more opaque. A lack of transparency slightly affects the detectability of defects. If the oil phase in the microemulsion forms the dispersed phase, water forms the continuous phase and there is an oil-in-water microemulsion (O/W microemulsion). There are conversely water-in-oil microemulsions, (W/O microemulsions).

Microemulsions are often not emulsions with particularly small droplets of the dispersed phase, but rather thermodynamically stable liquid mixtures of water, water-insoluble substance and surfactant. Thermodynamic stability, spontaneous formation, and optical transparency are often what differentiates microemulsions from emulsions. Their characteristics often include isotropy, clarity, transparency and/or slight opalescence, thermodynamic stability and low viscosity. They have a high transparency and are often also stable upon centrifugation at 2000 rpm for at least 30 minutes with respect to a visible phase separation.

Microemulsions may be subject to a strong dynamic which can lead to continuous assembly and disassembly processes of the aggregates due to fluctuation of individual molecules. Microemulsions can invert, like conventional emulsions, if the phase volume ratio is altered.

Microemulsions are often permanently stable and can often form spontaneously. Microemulsions may be single phase, or may be present with one or two other phases. These two additional phases consist of aqueous or of water-insoluble organic phases. A microemulsion typically contains, in addition to the two non-miscible liquids, at least one surfactant. This may contribute to the formation of micelles. The micelles take up this second, immiscible liquid. Once the absorption capacity of the micelles is exhausted, the rest of the second liquid may form excess phases. Then there can potentially be two different substantially water-insoluble liquid phases C). When one surfactant alone in the composition is not sufficient to form a microemulsion, it is recommended that at least one further surfactant is added, as a co-surfactant, and/or at least one co-solvent is added, such as to add least one medium-chain alcohol. A single-phase microemulsion often arises only given a sufficiently high content of surfactant.

The problem is addressed with a use of a penetrant testing medium for defect detection according to the penetrant method, in particular for metallic and/or non-metallic components, which is characterized in that it is a microemulsion which comprises:

A) at least 10 wt %, of water A),
B) at least 0.1 wt % of at least one dye B) which has a solubility in water of less than 0.1 g/L at 20° C. and atmospheric pressure, and which is optionally present in a dye system,
C) at least 5 wt % of at least one substantially water-insoluble liquid phase C), wherein the solubility of the substantially water-insoluble, or water-insoluble, organic compounds of the substantially water-insoluble phase C) is at most 60 g/L in distilled water at 20° C. and atmospheric pressure, and
D) at least 2 wt % of at least one surfactant D) selected from nonionic, anionic and/or amphoteric surfactants, also optionally containing at least one additive E).

wherein optionally a dye system containing a dye B) is also included at 0.11 to 20 wt %, wherein the sum of all the constituents is 100 wt %, is 100 wt %, wherein the penetrant testing medium has an average particle size ranging from 1 to 250 nm measured with a Malvern Zetasizer Nano ZS and a transparency of at least 70% at 600 nm in a quartz cuvette and for a 10 mm thickness of the irradiated liquid, at a temperature of 20° C. at atmospheric pressure, measured by a Hach Lange GmbH CADA 100-V photometer using a microemulsion which is the same but does not contain any dye, except for yellow fluorescent penetrant testing media.

The sum of the constituents A), B), C) and D) does not have to be 100%—for example if at least one additive E) is included and the components A). B), C) and D) only add up to 100% if said additive is included. For all of the compositions, the word "contain" can also be replaced with "substantially consist of" or "comprise" if necessary.

The average particle size is measured in this case using a microemulsion containing a dye—unlike the measurements for, optionally, transparency. This because, for red-white testing and for red fluorescent penetrant testing media, the particle size is only measured using a microemulsion containing no dye, since the dye intensity of the red dye is too strong.

It is preferred in this case that there is an oil-in-water microemulsion (O/W) or water-in-oil microemulsion (W/O), in which, instead of oil, or together with oil, at least one other fluid which is immiscible with water is used. Preferably, the microemulsion according to the invention contains, as an O/W microemulsion, at least 30 wt % of water A), and as a W/O microemulsion, least 10 wt % of water A).

The penetrant testing medium according to the invention is preferably an O/W microemulsion in the case of yellow or red fluorescent penetrant testing media, containing A) 30 to 85 wt % of water A),
B) 0.1 to 10 wt % of at least one dye B) which has a solubility in water of less than 0.1 g/L at 20° C. and atmospheric pressure, and which is optionally present in a dye system,
C) 5 to 50 wt % of at least one substantially water-insoluble liquid phase C),
D) 2 to 60 wt % of at least one surfactant D), and optionally also at least one additive E),
wherein optionally a dye system containing a dye B) is also included at 0.11 to 20 wt %,
wherein the weight ratio of the C) fraction to the D) fraction, is optionally in the range from 0.08:1 to 25:1, from 0.14:1 to 8:1, from 0.2:1 to 6:1, from 0.3:1 to 4:1, or from 0.6:1 to 2:1,
wherein the sum of all the constituents is 100 wt %, and
wherein the penetrant testing medium has an average particle size in the range from 1 to 250 nm as well as a transparency of at least 70% at 600 nm.

It is particularly preferred that it contains in this case
A) 40 to 75 wt % of water A),
B) 0.1 to 10 wt %/o of at least one dye B) which has a solubility in water of less than 0.1 g/L at 20° C. and atmospheric pressure, and which is optionally present in a dye system.
C) 7 to 40 wt % of at least one substantially water-insoluble liquid phase C), and
D) 5 to 50 wt % of at least one surfactant D).

The penetrant testing medium according to the invention is preferably an O/W microemulsion for red-white testing, containing
A) 30 to 80 wt % of water A).
B) 0.1 to 10 wt % of at least one dye B) which has a solubility in water of less than 0.1 g/L at 20° C. and atmospheric pressure, and which is optionally present in a dye system,
C) 5 to 45 wt % of at least one substantially water-insoluble liquid phase C),
D) 2 to 55 wt % of at least one surfactant D), and optionally also at least one additive E),
wherein optionally a dye system containing a dye B) is also included at 0.11 to 20 wt %,
wherein the weight ratio of the C) fraction to the D) fraction, is optionally in the range from 0.08:1 to 25.1, from 0.14:1 to 8.1, from 0.2:1 to 6:1, from 0.3:1 to 4:1, or from 0.61 to 2:1,
wherein the sum of all the constituents is 100 wt %, and wherein the penetrant testing
medium has an average particle size in the range from 1 to 250 nm as well as a transparency of at least 70% at 600 nm.

It is particularly preferred that it contains in this case
A) 30 to 70 wt % of water A),
B) 0.1 to 10 wt % of at least one dye B) which has a solubility in water of less than 0.1 g/Lat 20° C. and atmospheric pressure, and which is optionally present in a dye system,
C) 7 to 40 wt % of at least one substantially water-insoluble liquid phase C), and
D) 5 to 45 wt % of at least one surfactant D).

The penetrant testing medium according to the invention is preferably an O/W microemulsion in the case of yellow or red fluorescent penetrant testing media, containing A) 10 to 60 wt % of water A),
B) 0.1 to 10 wt % of at least one dye B) which has a solubility in water of less than 0.1 g/L at 20° C. and atmospheric pressure, and which is optionally present in a dye system,
C) 5 to 40 wt % of at least one substantially water-insoluble liquid phase C), and
D) 2 to 50 wt % of at least one surfactant D), and optionally also at least one additive E),
wherein optionally a dye system containing a dye B) is also included at 0.11 to 20 wt %,
wherein the weight ratio of contents of C):D) if appropriate, in the range of 0.08:1 to 25:1, from 0.14:1 to 8:1, from 0.2:1 to 6:1, from 0.3:1 to 4:1 or from 0.6:1 to 2:1,
wherein the sum of all the constituents is 100 wt %, and
wherein the penetrant testing medium has an average particle size in the range from 1 to 250 nm as well as a transparency of at least 70% at 600 nm.

It is particularly preferred that it contains in this case
A) 20 to 50 wt % of water A),
B) 0.1 to 10 wt % of at least one dye B) which has a solubility in water of less than 0.1 g/L at 20° C. and atmospheric pressure, and which is optionally present in a dye system,
C) 10 to 35 wt % of at least one substantially water-insoluble liquid phase C), and
D) 10 to 50 wt % of at least one surfactant D).

The penetrant testing medium according to the invention is preferably an O/W microemulsion for red-white testing, containing
A) 10 to 60 wt % of water A),
B) 0.1 to 10 wt % of at least one dye B) which has a solubility in water of less than 0.1 g/L at 20° C. and atmospheric pressure, and which is optionally present in a dye system, C) 5 to 40 wt % of at least one substantially water-insoluble liquid phase C), and
D) 2 to 40 wt % of at least one surfactant D), and optionally also at least one additive E).
wherein optionally a dye system containing a dye B) is also included at 0.11 to 20 wt %,
wherein the weight ratio of the C) fraction to the D) fraction, is optionally in the range from 0.08:1 to 25:1, from 0.14:1 to 8:1, from 0.2:1 to 6:1, from 0.3:1 to 4:1, or from 0.6:1 to 2:1,
wherein the sum of all the constituents is 100 wt %, and
wherein the penetrant testing medium has an average particle size in the range from 1 to 250 nm as well as a transparency of at least 70% at 600 nm.

It is particularly preferred that it contains in this case
A) 20 to 50 wt % of water A),
B) 0.1 to 10 wt % of at least one dye B) which has a solubility in water of less than 0.1 g/L at 20° C. and atmospheric pressure, and which is optionally present in a dye system,
C) 10 to 35 wt % of at least one substantially water-insoluble liquid phase C), and
D) 10 to 50 wt % of at least one surfactant D).

The microemulsion according to the invention will frequently have an average particle size in the range from 1 to 250 nm, from 1 to 200 nm, from 1 to 150 nm, from 1 to 100 nm, or from 1 to 40 nm, and a transparency of at least 70%, at least 80%, or at least 90% measured at 600 nm. The average particle size is measured with a Zetasizer Nano ZS from Malvern. The transparency is measured at 600 nm in a quartz cuvette, for a 10 mm thickness of the irradiated liquid, at 20° C. at atmospheric pressure, measured by a Hach Lange GmbH CADA 100-V photometer using a microemulsion which is the same but does not contain any dye, except in the case of yellow fluorescent penetrant testing media. If the dispersion is a cleaved microemulsion or an emulsion, it will frequently have an average particle size in the range of 80 to 1500 nm or in the range of 105 to 800 nm, as well as a transparency of at most 20%, or of at most 5%, at 600 nm—both measured as indicated above. However, they can then have a very low transparency as well. The penetrant testing media of the prior art, however, are clear solutions that show an average particle size below 1 nm, and—if it is possible to determine—a transparency greater than 90%.

The average particle sizes of the microemulsions according to the invention are less than 250 nm. The microemulsions according to the invention are preferably clear or transparent. In particular, the microemulsions according to the invention show a transparency of >75%, >80%, >85%, >90% or >94% at 20° C. at atmospheric pressure, with transparency values typically greater than 80% for microemulsions at 20° C. Particularly preferred are microemulsions which have a transparency, measured at 20° C. at atmospheric pressure, of 90 to 100%. In particular, microemulsions have a transparency of greater than or equal to 40% at 40° C. at atmospheric pressure, and transparency values of greater than 80% are typical for microemulsions at 40° C. Particularly preferred are microemulsions which have a transparency, measured at 40° C. at atmospheric pressure, from 85 to 100%.

The average particle sizes of the microemulsions according to the invention preferably lie in the range from 0.1 to 300 nm, more preferably in the range from 1 to 250 nm, from 1.5 to 200 nm, from 1.6 to 150 nm, from 1.8 to 120 nm, from 1.9 to 100 nm or from 2 to 80 nm. The microemulsions according to the present invention preferably exhibit particle sizes of less than 250 nm. The particle sizes of the micro emulsions of the invention are preferably less than 250 nm, particularly preferably in the range from 1 to 250 nm, from 1.5 to 200 nm, from 1.6 to 150 nm, from 1.8 to 120 nm, from 1.9 to 100 nm or from 2 to 80 nm. The particle sizes and the resulting calculated average particle sizes can be measured according to the invention with a Zetasizer Nano ZS from Malvern.

Other than the primary peak, the substantially single-peak particle size distributions have no secondary peak of more than 25% peak area as compared to the total area. Where multi-peak particle size distributions occur, only so-called "average particle sizes" are listed in the tables for peaks of at least 25% peak area. The results of the peak area calculations are output from the device being used. For this reason, up to three "average particle sizes" are listed for multi-peak particle size distributions in individual examples, all of which have a peak area greater than 25% of the total area.

In addition, the luminosity of the yellow fluorescent penetrant testing media can be tested, as fluorescence luminosity with an NDT Italiana fluorophotometer type S-291. It was measured in % against the reference Sherwin RC-77 Batch No. 92-B15. Here, particular values were in the range from 50 to more than 100% as compared to a FP-4PE Sherwin reference system, measured using dried dye films of the penetrant testing medium or reference solution on a standardized filter paper. The penetrant testing media can be divided into sensitivity levels in accordance with ISO 3452 with respect to the percentage of fluorescence luminosity of the dried dye film by a visual comparison with an identically and simultaneously produced reference pattern i: level ½— at least 500, level 1—at least 65%, level 2—at least 80%, level 3—at least 90, and level 4—at least 95%. Preferably, the penetrant testing medium according to the invention has a luminosity of at least 60%, at least 900% or even more than 100%. However, these methods of measurement have a significant uncertainty. Nevertheless, luminosity has been used as a characteristic feature for a long time.

A microemulsion according to the present invention is a dispersion with a disperse phase which forms such small domains—in particular as droplets, tubes and/or layers— that visible light is not or almost not scattered by them. It is usually transparent or clear. A Tyndall effect was not observed in dye-free dispersions of very small particle sizes, but appeared above approximately 70 nm average particle size, at least as a weak effect.

The penetrant testing medium can preferably be characterized in that the dispersion is an oil-in-water microemulsion (O/W).

Alternatively, the penetrant testing medium according to the invention is preferably characterized in that the dispersion is a water-in-oil microemulsion (W/O), in which at least one other liquid which is not soluble in water is optionally used in place of oil or together with oil, such as, by way of example, organic solvents which are insoluble or substantially insoluble in water, as the substantially water-insoluble phase C), which are liquid under the given conditions, such as carboxylic acid esters, ethers and/or unsubstituted hydrocarbons, for example.

In a O/W microemulsion, the content of the substantially water-insoluble phase C) preferably ranges from 5 to 50 wt %, from 5 to 45 wt %, from 7 to 40 wt %/o, from 10 to 35 wt %, or from 15 to 30 wt % and the amount of surtactants D) is preferably in the range from 2 to 60 wt %, from 2 to 55 wt %, from 5 to 50 wt % b, from 5 to 45 wt %, from 8 to 40 wt %, or from 10 to 35 wt % In contrast, in a W/O microemulsion, the content of the substantially water-insoluble phase C) preferably ranges from 5 to 40 wt %, from 8 to 40 wt %, from 10 to 35 wt %, from 12 to 30 wt %, or from 15 to 30 wt %, and the amount of surfactants D) is preferably in the range from 2 to 50 wt %, from 10 to 50 wt %, from 3 to 45 wt %, from 2 to 40 wt %, from 10 to 35 wt %, or from 15 to 30 wt %.

All transitions are fundamentally possible in the large region between O/W and W/O microemulsions, and often occur fluently. When an O/W or a W/O emulsion or a O/W or a W/O microemulsion is formed, the additives can be substantially dependent on the type and/or amount of the substances used in the substantially water-insoluble phase C), on the type and/or amount of surfactants used D), optionally including the type and/or amount of the surfactants D) optionally functioning as co-surfactants and/or emulsifiers, and/or the type and/or amount of the solubilizers used.

In penetrant testing media according to the invention, an O/W microemulsion in the sensitivity levels from 0.5 to 3 is preferred. In yellow fluorescent penetrant testing media according to the invention, an W/O microemulsion in the sensitivity level 4 is preferred. The sensitivity levels of yellow fluorescent penetrant testing medium microemulsions according to the invention usually range from 0.5 to 4, wherein 4 is the most sensitive penetrant testing medium. The inventive microemulsions for red-white testing and red fluorescent penetrant testing media can usually be assigned to sensitivity level 2, wherein there are only two levels: level 1, for low and level 2 for high sensitivity. With the penetrant testing media according to the invention, it is possible to reach all sensitivity ranges according to characteristic profile, wherein the amount of the particular yellow fluorescent dyes significantly affects the product cost.

An O/W microemulsion is preferable for especially environmentally friendly penetrant testing media. Particularly for the yellow fluorescent penetrant testing media, an O/W microemulsion is preferred for penetrant testing media with an extended working temperature range, for example from 5 to 90° C. In this case, there are compositions which are a microemulsion at room temperature and an emulsion at 50° C., as shown in individual examples. They usually have a non-ionic surfactant with a lower clouding point. When non-ionic surfactants are used, the solubility for the substantially water-insoluble solvents C) of the surfactants decreases because of the decreasing degree of hydration as temperature increases (=clouding point).

The penetrant testing medium of the present invention preferably has average particle sizes no greater than 200 nm, greater than 100 nm, greater than 50 nm, greater than 20 nm or greater than 10 nm, measured with a Malvern Zetasizer Nano-ZS, using software version 6.20, at 25° C. in a quartz cuvette with a layer thickness of 10 mm, wherein the samples are measured directly without any further preparation. In each case, at least 2 intervals, each with at least 10 measurements, were measured. Since the Zetasizer Nano-ZS heats itself to about 25° C., no further boundary conditions must be observed.

For the penetrant testing media according to the invention in the form of microemulsions, it is preferred that they cannot be visually distinguished from a solution due to the small size of the particles. Almost all the penetrant testing media according to the invention are clear as a solution. As a result of this, and together with a higher dye content, a slightly higher defect detectability is obtained. The penetrant testing medium according to the invention can be characterized for example by dynamic light scattering in particle size measuring devices. In this case, "normal" dispersions are often characterized by average particle sizes (=average droplet sizes) of more than 300 and up to about 100,000 nm. Here, emulsions are characterized by mean droplet sizes (particle sizes) greater than 100 and up to 100,000 nm, and microemulsions by mean particle sizes in the range from 1 to about 250 nm. Particularly preferred are average particle sizes of less than 100 nm or less than 70 nm.

With regard to transparency, emulsions are characterized by a transparency in the range from 0 up to about 10% and microemulsions by a transparency at 600 nm in the range from 70 to 100%.

The preferred aim is therefore a stable and clear or transparent microemulsion. A microemulsion is particularly considered stable if no phase separation can be observed with the naked eye over at least one month, so that no droplets and no layers, no significant cloudiness in the microemulsion, and no or virtually no loss of clarity or transparency of the microemulsion can be observed.

A stable microemulsion is obtained in some compositions only when the substances which are necessary for the formation of the microemulsion, namely in particular water, the substantially water-insoluble phase C), surfactant, and optionally co-surfactant are present in a certain volume ratio. This volume ratio is essentially determined by the nature of the surfactants D) and the substantially water-insoluble phase C). If there is an appropriate volume ratio, a stable single-phase mixture usually forms as a microemulsion without additional energy input, for example without intensive mixing and without intensive stirring.

Preferably, the mix ratio of water A) to substantially water-insoluble phase C) is in the range from 0.25:1 to 17:1, from 0.60:1 to 17:1, of 0, 40.1 to 12.1, of 0, 30:1 to 10:1, of 0, 40:1 to 9:1, from 0.50:1 to 8:1, from 0.55:1 to 5:1, 0.60:1 to 6:1, from 0.65:1 to 16:1, from 0.75:1 to 10:1, from 0.80:1 to 5.1, from 1.1 to 1 1:1, of 1:1 to 4:1 or from 2:1 to 3:1, based on the weight ratio of water A) to surfactants D).

Preferably, the mix ratio of water A) to surfactants D) is, including the surfactants D) optionally acting as co-surfactants and/or emulsifiers, in the range from 0.2:1 to 42.5:1, of 0.25:1 to 30:1, of 0.3:1 to 20:1, of 0.4:1 to 10:1, from 0.5:1 to 8:1, from 0.6:1 to 6:1, from 0.8:1 to 5:1, from 1:1 to 4:1 or from 2:1 to 3:1, based on the weight ratio of water A) to surfactants D).

The stability of these single-phase mixtures is are often highly dependent on temperature when non-ionic surfactants are used, because due to the degree of hydration which falls with increasing temperature, cleaving of an emulsion or microemulsion can occur. In contrast, when surfactants are used which have a hydration rate which is less temperature-dependent than, for example, with anionic surfactants, microemulsions are usually obtained which are stable in a wide temperature range, such as from 5 to 60° C. for example. The temperature dependence is frequently shown upon heating by a clouding of the penetrant testing medium, up to a complete breaking of a microemulsion, which is often clearly visible by phase separation. Particularly in the working temperature range of 10 to 50° C. as specified by the relevant specifications such as the AMS 2644 or DIN EN ISO 3452-2, a division of the penetrant testing medium is undesirable. When non-ionic surfactants are used, they are preferably those having a clouding point of more than 50° C., of more than 60° C. or of more than 70° C.

The microemulsion according to the invention is preferably clear or transparent. Preferably, the microemulsion according to the invention shows neither clouding nor clouding with a strong Tyndall effect. A Tyndall effect can occur particularly in the case of fluorescent penetrant testing media regardless of the average particle size, in the presence of dye, and can occur in dye-free dispersions having average particle sizes larger than about 70 nm average particle size.

Preferably, the microemulsion according to the invention contains, as an O/W microemulsion, at least 30 wt % of water A), and as a W/O microemulsion, at least 10 wt % of water A). Preferably, the microemulsion according to the invention contains, as an O/W microemulsion, at least 25 wt %, at least 30 wt %, at least 35 wt %, at least 40 wt %, at least 45 wt %, at least 50 wt % at least 55 wt %, or at least 60 wt %, or from 25 to 80 wt %, from 30 to 75 wt %, from 35 to 70 wt %, from 40 to 65 wt %, or from 45 to 60 wt %, of water A).

The penetrant testing medium according to the invention preferably contains, as a W/O microemulsion, at least 15 wt %, at least 20 wt %, at least 25 wt %, at least 30 wt %, at least 35 wt %, at least 40 wt %, or at least 45 wt %, or from 15 to 60 wt %, from 20 to 55 wt %, from 25 to 50 wt %, from 30 to 45 wt %, or from 32 to 40 wt %, of water A).

For penetrant testing media based on yellow or red fluorescent O/W microemulsions, the water content A) is preferably in the range from 32 to 80 wt %, in the range from 35 to 75 wt %, in the range from 40 to 70 wt %, in the range from 45 to 65 wt %, or in the range from 48 to 60 wt %. For penetrant testing media for red-white testing, based on O/W microemulsions, the water content A) is preferably in the range from 32 to 80 wt %, in the range from 25 to 75 wt %, in the range from 30 to 70 wt %, in the range from 35 to 65 wt %, or in the range from 40 to 60 wt %.

For penetrant testing media based on yellow or red fluorescent W/O microemulsions, the water content A) is preferably in the range from 10 to 60 wt %, in the range from 15 to 55 wt %, in the range from 20 to 50 wt %, in the range from 25 to 45 wt %, or in the range from 30 to 42 wt %.

For penetrant testing media for red-white testing, based on W/O microemulsions, the water content A) is preferably in the range from 10 to 60 wt %, in the range from 15 to 55 wt %, in the range from 20 to 50 wt %, in the range from 25 to 45 wt %, or in the range from 30 to 42 wt %.

If the water content of the penetrant testing media according to the invention is less than 30 wt %, for yellow or red fluorescent penetrant testing media and/or less than 10 wt % for penetrant testing media for red-white testing, the penetrant testing medium is less environmentally friendly. If the water content of the penetrant testing media according to the invention is more than 95 wt %, or is too high for the respective microemulsion, the penetrant testing medium is less sensitive and the defect detection is poorer.

The penetrant testing medium according to the invention comprise B) at least one dye B) having a solubility in water of less than 20 g/L and particularly less than 0.1 g/L at 20° C. at atmospheric pressure, wherein said can optionally be part of a dye system. The water solubility of the dyes for the penetrant testing medium according to the invention is less than 0.1 g/L at 20° C. at atmospheric pressure; specifically, for example, rhodamine B (Solvent Red 49) has a water solubility of about 15 g/L at 20° C. at atmospheric pressure. The dye is necessary to enable detection of defects. In principle any dye can be used which has such a low water solubility, and which allows a sufficiently high contrast— such as red, green, blue or black. Dye mixtures, such as red and blue, can also be used to achieve certain dye colors. The AMS 2644 standard limits the choice of dyes to orange, red and violet. Particularly preferred dyes B) are red, because the human eye is particularly sensitive to red dye. Particularly preferred are red dyes B) from the CI (Color Index) Solvent Dyes series, an internationally recognized classification of dyes and pigments. Very strongly preferred red dyes B) are CI Solvent Red dyes with the numbers 1, 23, 24, 26, 111, 164, 197, 229 and/or 242. In this case, Solvent Red 49, based on xanthene dye, can be used as a fluorescent red dye B). The AMS 2644 standard relates to fluorescent dyes with green, yellow or orange fluorescence emission. Preferred are Solvent Yellow 43, Disperse Yellow 199, Solvent Green 5, and/or Solvent Green 7, optionally with a fluorescence intensifier such as a coumarin and/or a stilbene.

The dye B) can particularly be dyes which are not, or are only sparingly, soluble in water at 20° C. and which are readily soluble in a substantially water-insoluble liquid phase C), especially those having a solubility at 20° C. of at least 10 g/L in the substantially water-insoluble phase C) or in the substantially water-insoluble phase C) and in at least one surfactant D). The dye B) and/or the dye system is/are often a mixture of multiple substances B). It is, for example, selected from anthraquinones, azomethine dyes, azo dyes without metal complex, metal complex dyes such as, for example, azo-metal complex dyes, formazans and/or phthalocyanines, benzodifuranones, chinacridones, dioxazines, methine dyes, naphthalimides, perylenes, polymethine dyes, triphenedioxazines, triphenylmethane dyes and/or xanthenes.

Particularly preferred as dye B) is at least one dye selected from the group consisting of anthraquinones, azo dyes, azo-metal complex dyes, azomethines, methine dyes, naphthalimides, polymethine dyes, triphenedioxazines, triphenylmethane dyes and/or xanthenes.

The dyes Solvent Yellow 43, coumarin and fluorescein are preferably used for fluorescent testing with yellow compositions, while dyes based on Solvent Red always are always used for red and white penetrant testing media. When rhodamine B (neptune Red Base 546 from BASF) is used, red fluorescent penetrant testing media are obtained.

Instead of a single dye B), a dye system can also be used. The at least one dye B) can then preferably be contained in a dye system which optionally contains at least one brightener, which often acts as a fluorescence amplifier and thus as a dye enhancer, at least one dye additive and/or at least one further dye and/or dye B) which works differently with respect to the fluorescence. In this case, the at least one dye B) can optionally consist of a plurality of individual dyes, especially to achieve a particular dye color, particularly in the case of commercially available products as well. Furthermore, the at least one dye B) can be present as a solution in a suitable solvent, for example in at least one solvent based on mineral oil, alcohol and/or glycol. In addition, such dye preparations can optionally also contain at least one dye additive selected from among additives such as suspending agents, emulsifiers, dispersing agents and/or preservatives. The dyes are often commercially available in the form of a solution in at least one organic solvent which can typically absorb the dye with at least a solubility of 20 g/liter at 20° C., such as at least one mineral oil, glycol and/or glycol ether in each case, for example. Coumarins and/or stilbenes can be used as brighteners for fluorescent dyes B), for example. Preferably, the at least one brightening agent is dissolved in at least one substance in the substantially water-insoluble phase C) or in the entire phase C).

Brighteners are highly soluble in at least one substance in the substantially water-insoluble phase C). For faster dissolving of coumarin solid, it can be advantageous to use a higher concentration of phase C) or a higher concentration of at least one substance in the substantially water-insoluble phase C) which dissolves the coumarin particularly well. If several individual dyes B) or a dye system are used in a mixture, it is possible that the individual substances are more or less well dissolved in the substantially water-insoluble phase C), in particular depending on the selection of substances of the substantially water-insoluble phase C) and their amounts, such that it is advisable to use a mixture of substances in the substantially water-insoluble phase C), wherein at least one substance of this mixture C) dissolves at least one substance of the dye B) and/or at least one brightener and/or at least one dye additive particularly well.

An undissolved dye B) can, by way of example, be present in the form of a solid, preferably in amorphous and/or crystalline form, and can then preferably be incorporated by being dissolved in the substantially water-insoluble phase C). The penetrant testing medium according to the invention preferably has an amount of at least one fluorescent dye B), at least one dye B) with a color in the visible light region, at least one dye B) which has a color in the visible light region and fluoresces, and/or at least one dye B) detectable under UV Light. If neither a fluorescent dye nor a dye which can be detected under UV light is used, a red dye B) is preferably is added because the human eye is particularly sensitive to the red dye.

When a fluorescent dye B) is used, in some embodiment variants, a testing process is employed, with or without a developer, in which case a white or colorless developer is used which preferably also draws the fluorescent dye to the surface, thereby improving the visibility.

This developer is applied separately after the application of the penetrant testing medium according to the invention. The developer should draw the composition containing the dye B), the same having penetrating into a defect, and optionally present the same more clearly in color contrast to the white developer.

When a red dye B) is used, in one variant the red-white testing methods can preferably be used, employing a white developer. In another embodiment, the red dye B) is used either with or without a white developer. The developer can be fine-crystalline, amorphous and/or microporous, organic and/or inorganic solids of white paint, and/or colorless, such as carbonates, oxides, silicates and/or organic solids, which are preferably at least partially solid in the temperature range from 10 to 50° C. They are generally soluble neither in water nor in organic solvent in amounts of at least 1 g/L at 20° C. These include, by way of example, alkaline earth metal oxides, aluminum oxides, silicas, titanium dioxides, bentonites, talc, compounds of benzoic acid such as salts thereof, cellulose, cellulose derivatives, pentaerythritol and/or polyalkylene glycols.

The penetrant testing medium according to the invention preferably contains at least one dye B) which is substantially insoluble or completely insoluble in water.

The penetrant testing medium according to the invention contains B) at least 0.1 wt % from 0.1 to 20 wt %, or from 0.55 to 15 wt %, of at least one dye B). It is particularly preferred that it contains at least 0.5 or at least 3 wt % of at least one dye B), or 1 to 20 wt % or from 3 to 15 wt % of at least one dye B), and most preferably of all at least 5 or at least 6 wt % of at least one dye B), or from 5 to 12 wt % or from 7 to 10 wt %, of at least one dye B), wherein the dye can preferably be contained up to the solubility limit at 20° C. in the substantially water-insoluble phase C) or in the phase C, and in at least one surfactant D). The brightener can be found in the dye system, preferably in a range from 0.01 to 8 wt %, or in the range from 0.5 to 4 wt %. The amount thereof is usually higher than the amount of dyes B). A dye system is preferably used if testing will be carried out with fluorescence under UV light. For the dyes B), azomethines and/or naphthalimides for the fluorescent applications, and/or anthraquinones, azo dyes, azo-metal complex dyes, methine dyes, polymethine dyes, triphenylmethane dyes and/or xanthenes for the range of visible light are particularly preferred. However, there are also individual dyes B) which can be used in the range of visible light and which also fluoresce when exposed to UV light, and which can be used for testing in one of the two types of light or simultaneously with the two types of light, such as CI Solvent Red 49. A particularly preferred dye system is a fluorescent mixture of an azomethine or a napthalimide, in each case with a brightening agent based on coumarin or stilbene.

If the penetrant testing medium according to the invention contains less than 0.1 wt % of at least one dye B), the penetrant testing medium is not sufficiently sensitive and the defect detection is worse. If the penetrant testing medium according to the invention contains more than 10 wt % of at least one dye B), this usually exceeds the solubility limit for the dye. On the other hand, the penetrant testing medium according to the invention can be adjusted, in the case of a lower water content, in such a manner that more water insoluble and/or substantially water-insoluble dye B) is dissolved, and thereby the sensitivity of the penetrant testing medium and the defect detection can be improved.

If the penetrant testing medium according to the invention contains less than 0.1 wt % of at least one dye, or less than 0.11 wt % of at least one dye system, the penetrant testing medium is not sufficiently sensitive and the defect detection is worse. If the penetrant testing medium according to the invention contains more than 20 wt % of at least one dye or a dye system, the solubility limit is often exceeded for the dye B).

Moreover, it is possible to use at least one substantially water-insoluble organic solvent in the penetrant testing medium according to the invention, in which the at least one dye B) or the selected dye system can be dissolved as completely as possible, or completely, preferably without very high content of surfactant, in particular with a content of surfactant D) of less than 40 wt %, completely dissolved or dissolved as completely as possible in at least one compound of the substantially water-insoluble phase C) If the dye or the dye system of the penetrant testing medium according to the invention is completely dissolved, no cloudiness and no precipitation occurs in the range from 10 to 50° C.

This is another advantage, because a high level of surfactant is environmentally harmful and can easily lead to the penetrant testing medium washing out of cracks and other defects. In this way, the penetrant testing medium according to the invention enable a higher concentration of the dye or the dye system in the penetrant testing medium, thereby providing an improved display of defects and an increase in sensitivity compared to penetrant testing media with a lesser amount of dye or dye system.

The penetrant testing medium according to the invention contains at least 5 wt %, or in the range from 5 to 50 wt %, of at least one compound of the substantially water-insoluble phase C) which is liquid at 20° C. at atmospheric pressure. This substantially water-insoluble phase C) is largely present as a mixture of several substances C). If the substantially water-insoluble phase C) consists of more than one substance, these are usually miscible with one another. It essentially corresponds to the oil phase of the O/W or W/O microemulsion. This serves in particular as a solvent for at least one dye B) and/or for at least one further component of the dye system, such as for at least one brightener. In addition, it can be possible that the substantially water-insoluble phase C) also dissolves other components such as corrosion inhibitors and/or preservatives, for example. It can optionally influence the surface tension of the penetrant testing medium, and in particular reduce the same. In the following, the at least one compound of the substantially water-insoluble phase C) which is liquid at 20° C. at atmospheric pressure is particularly termed "phase C)".

The penetrant testing medium according to the invention is preferably characterized in that the substantially water-insoluble liquid phase C) contains at least one organic compound which is liquid at 20° C. at atmospheric pressure, and which is selected from among the group consisting of hydrocarbons, including "petroleum products" C1), alcohols C2), esters and/or amides of mono-, di- and/or polycarboxylic acids C3), phosphoric esters C4), ethers C5), ketones C6), oils and their derivatives, C7)—which are not "petroleum products"—and ether/ester derivatives of diols and polyols C8), or is selected from among the group consisting of alcohols C2), esters and/or amides of mono-, di- and/or polycarboxylic acids C3), ethers C5) and ketones C6).

The amount of the substantially water-insoluble phase C) is preferably at least 7 wt %, at least 9 wt %, at least 11 wt %, at least 15 wt %, or at least 15 wt %, at most 50 wt %, at most 40 wt %, at most 30 wt %, at most 25 wt %, or in the range from 5 to 50 wt %, in the range from 5 to 45 wt %, in the range from 5 to 40 wt %, in the range from 7 to 40 wt %, in the range from 10 to 35 wt %, in the range from 13 to 40 wt %, in the range from 15 to 30 wt %, or in the range from 18 to 25 wt %, wherein the amount range can vary significantly according to the type of microemulsion and the penetrant testing medium.

The solubility of the substantially water-insoluble, or water-insoluble, organic compounds of the substantially water-insoluble phase C) is, at 20° C. at atmospheric pressure, preferably at most 60 g/L in distilled water, preferably at most 50 g/L, at most 40 g/L, at most 30 g/L or at most 20 g/L. The solubility of the mixture of substantially water-insoluble, or water-insoluble, organic compounds of the substantially water-insoluble phase C) is, at 20° C. at atmospheric pressure, preferably at most 60 g/L in distilled water, preferably at most 50 g/L, at most 40 g/L, at most 30 g/L or at most 20 g/L. However, this value which appears high means that, if the volume of the liquid phase C) is high, for example 30 wt %, of the approximately 300 g/l of this liquid phase C) a high proportion of water is contained undissolved in the penetrant testing medium.

In principle, many organic solvents can be selected as components of the phase C) which is liquid at room temperature and substantially water-insoluble. It is particularly preferred that the phase C) which is liquid at room temperature dissolves the desired dye B) to the greatest extent possible, particularly in a range of 10 to 300 g/L, more preferably from 20 to 200 g/L, and/or is particularly environmentally friendly.

However, in the context of the invention, the volume of a surfactant which can serve as the organic solvent at the same time is only considered as a surfactant and not as a solvent of a substantially water-insoluble liquid phase C), although it also has a function as an organic solvent.

The substantially water-insoluble phase C) of the penetrant testing medium according to the invention contains at least one substance which can be dissolved in water at 20° C. at atmospheric pressure at most to 60 g/L. Preferably, this at least one substance can be dissolved in water, at 20° C. at atmospheric pressure, to a maximum of 50 g/L, to not more than 40 g/L, to not more than 30 g/L, to not more than 20 g/L, to more than 10 g/L, to not more than 1 g/L, or essentially not at all. Each substance contained in the substantially water-insoluble phase C) preferably has such a solubility in water. Therefore, the substance, or all substances, contained in the substantially water-insoluble liquid phase C) has/have a solubility in water at 20° C. at atmospheric pressure in the range from 0 to 60 g/L, from 0.1 to 50 g/L, from 1 to 40 g/L, from 5 to 30 g/L or from 10 to 20 g/L.

This at least one compound of the substantially water-insoluble liquid phase C) can be selected from the group of organic substances which are water-insoluble and substantially water-insoluble, and are liquid at 20° C. at atmospheric pressure, consisting of hydrocarbons, including "petroleum products" C1), alcohols C2), esters and/or amides of mono-, di- and/or polycarboxylic acids C3), phosphoric esters C4), ethers C5), ketones C6), oils and their derivatives C7) which are not "petroleum products", and combined ether-ester derivatives of diols and polyols C8). The at least one compound of the substantially water-insoluble phase C) contains in particular, or in particular comprises, aliphatic hydrocarbons having no functional group, aromatic hydrocarbons having no functional group, aliphatic esters, aromatic esters, aliphatic ethers, ethers, oils, glycol monoalkyl ethers and/or glycol diethers Particularly preferred is the use of at least one substance of the carboxylic acid esters C3) and/or of at least one substance of the ethers C5). In this case, the dialkyl esters of dicarboxylic acids with carbon chain lengths of the carboxylic acid in the range from 2 to 8 carbon atoms, in particular 4 to 6 carbon atoms, and/or the alkylene glycol monoalkyl ethers and/or alkylene glycol monoaryl ethers with carbon chain lengths of the alkylene glycol in the range from 2 to 8 carbon atoms, in particular 2 to 6 carbon atoms, are very particularly preferred. Preferably, the O/W microemulsions for yellow fluorescent penetrant testing media and the W/O microemulsions for red fluorescent penetrant testing media and penetrant testing media for red-white testing have no oil.

Examples of such hydrocarbons C1) in this case are i) aliphatic (acyclic) hydrocarbons, ii) aromatic hydrocarbons, iii) cycloaliphatic (alicyclic) hydrocarbons, and iv) "petroleum products" which contain mixtures of i, ii and/or iii from petroleum and/or contain the distillates thereof as mineral oils, the distillates thereof, and/or their individual components.

Examples for aliphatic hydrocarbons i) are linear or branched, saturated or unsaturated aliphatics, and particularly preferably aliphatic compounds having 5 to 16 carbon atoms, such as in particular pentane, hexane, octane, 2-ethyl hexane and/or 3,5,5-trimethylhexane.

Examples of aromatic hydrocarbons ii) are mono- or polyalkyl-substituted aromatic compounds such as, by way of example, those having one, two or three substituent alkyl-groups, each—independently of each other—having one to ten carbon atoms, such as, for example, benzenes like toluene, xylene, mesitylene, cumene, ethylbenzene and/or hydrocarbons with fused aromatic ring systems such as naphthalene, in particular 1-methylnaphthalene, 2-methylnaphthalene and dimethylnaphthalene, and/or asymmetrical or heterogeneous fused aromatic hydrocarbons such as, for example, indane and/or tetralin.

Examples of cycloaliphatic hydrocarbons iii) are saturated and/or unsaturated, optionally mono- or polyalkyl-substituted cycloaliphatic compounds such as those with one, two or three substituted alkyl groups, by way of example, each having—independently of each other—one to ten carbon atoms per alkyl-group, such as cyclohexane or methylcyclopentane. In this case, mixtures of one or more aliphatic hydrocarbons and/or one or more aromatic hydrocarbons and/or one or more alicyclic hydrocarbons are advantageous, for example commercially available solvents in the EXXSOL® D series, the SOLVESSO® series, or the ISOPAR® series from Exxon Mobil Chemicals.

Examples for iv) "petroleum products", which contain mixtures of i, ii and/or iii from petroleum and/or their distillates, their distillates, and/or their individual components, are, for example, mixtures of distilled crude oil fractions of petroleum, White Spirit D100, and/or isooctane. Examples of alcohols C2) are saturated or unsaturated, linear or branched, primary, secondary or tertiary, aliphatic, alicyclic, or aromatic alcohols, they preferably have 4 to 22 carbon atoms, such as in particular tert-butanol, 2-ethylhexanol, octanol, dodecanol or benzyl alcohol.

Examples of carboxylic acid derivatives C3) are the esters and/or annides of mono-, di- and polycarboxylic acids, such as tri- and tetracarboxylic acids, as well as higher-functional carboxylic acids, preferably carboxylic acids having 2 to 24 carbon atoms per alkyl chain.

Preferred esters C3) are the esters of alcohols i) having 1 to 20 carbon atoms, such as methanol, ethanol, isopropanol, isobutanol and/or 2-ethylhexanol, wherein for the fatty alcohols, glycerol and glycol esters are particularly preferred.

Examples of monocarboxylic acid esters ii) of the esters C3) are a) the esters of aliphatic and/or aromatic monocarboxylic acids, for example aliphatic monocarboxylic acid esters with alkyl chains of 1-9 carbon atoms, such as formic esters, acetic esters and propionic esters, b) aliphatic fatty acid esters such as monocarboxylic acid esters with alkyl-chains of 10-24 carbon atoms, which can be present in natural oils or vegetable oils or an be of synthetic origin, and/or c) aromatic monocarboxylic acid esters with alkyl chains of 7-24 carbon atoms, such as benzoic acid esters and phenylacetic acid esters.

Examples of fatty acid esters iii) of the esters C3) are those of natural origin, such as, for example, animal and vegetable oils, as well as those of synthetic origin; esters of fatty acids with alkyl-chains having 10 to 24 carbon atoms or 12 to 24 carbon atoms are particularly preferred as fatty acid esters. The fatty acid esters with alkyl-chains of 10 to 24 carbon atoms are, for example, esters of unsaturated or saturated fatty acids having alkyl chains from 10 to 24 carbon atoms, and are in particular those having an even number of carbon atoms, such as, for example, lauric acid, palmitic acid and in particular cis-fatty acids such as stearic acid, oleic acid, linoleic acid and linolenic acid. Further examples of fatty acid esters with alkyl chains of 10 to 24 carbon atoms are glycerol and glycol esters of fatty acids such as fatty acids having alkyl chains from 10 to 24 carbon atoms or their transesterification products, such as alkyl-fatty acid esters, in particular C1-C20 alkyl-C10-C24 fatty acid esters, such as, for example, such as those which can be obtained, for example, by transesterification of the above-mentioned glycerol and glycolic fatty acid esters, such as fatty acid esters with alkyl chains of 10 to 24 carbon atoms, with alcohols having 1 to 20 carbon atoms, such as, for example, methanol, ethanol, propanol and/or butanol. The transesterification can be carried out according to known methods such as those described in Römpp, "Chemie Lexikon", 9th Edition, Volume 2, Page 1343, Thieme Verlag Stuttgart. Preferred fatty acid esters are, for example, oils of oleaginous plant species such as soybean oil, rapeseed oil, corn oil, sunflower oil, cottonseed oil, linseed oil, coconut oil, palm oil, safflower oil, walnut oil, peanut oil, olive oil and/or castor oil, in particular rapeseed oil, wherein the vegetable oils also include their transesterification products, such as alkyl esters such as rapeseed oil methyl ester or rapeseed oil ethyl ester. Examples of dicarboxylic esters and polycarboxylic esters are the full esters of oxalic, malonic, succinic, glutaric, 2-methylglutaric, adipic, pimelic, sebacic, azelaic, suberic, maleic, phthalic, terephthalic-, mellitic-, trimellitic and polymaleic acids Particularly preferred are alkyl esters having alkyl chains of 1-10 carbon atoms, such as methyl esters, ethyl esters, n-propyl, iso-propyl, n-butyl, iso-butyl, sec-butyl or tert-butyl esters. Preferred dicarboxylic acid esters are the full esters of succinic, glutaric, 2-methylglutaric and adipic acid. Preferably, the alkyl esters have alkyl chains of 1-10 carbon atoms, such as methyl-, ethyl, or iso-butyl esters.

Preferred amides C3) are the N,N-dialkylamides of carboxylic acids having 6 to 20 carbon atoms, such as hexanoic acid, decanoic acid and stearic acid and their derivatives which do not have a high water solubility. Examples of carboxylic acid amides are aliphatic N,N-dialkylacylamides with a carbon chain length of the acyl moiety of 6-20 carbon atoms such as, for example, octanoic acid dimethylamide and decanoic acid dimethylamide.

Phosphoric acid esters C4) can be, for example, triesters of phosphoric acid with alcohols, wherein the alcohols are preferably selected from among the group comprising 1) monohydric alcohols having 1 to 22 carbon atoms, such as ethanol, isopropanol and 2-ethylhexanol, 2) diols and/or polyols such as ethylene glycol, propylene glycol and glycerin, 3) aryl, alkylaryl, poly(alkyl)aryl- and poly(arylalkyl) aryl alcohols such as phenol and/or cresol, octylphenol, nonylphenol, triisobutylphenol and tristyrylphenol, for example, and 4) alkoxylated alcohols obtained by reacting the alcohols named above under 1), 2) or 3) with alkylene oxides, and preferably with alkylene oxides with alkyl chains of 1 to 4 carbon atoms. Particularly preferred phosphoric acid esters are triesters of ortho-phosphoric acids such as triethylphosphate, tributylphosphate, and tri(butoxyethyl)phosphate.

By way of example, aromatic, cycloaliphatic and/or aliphatic ethers can be contemplated as ethers C5). Particularly preferred ethers are dialkyl ethers having alkyl chains of—independently of each other—3 to 12 carbon atoms, such as dihexyl ethers and dioctyl ethers or mono- and diethers of diols, and mono- or poly-alkoxylated diols such as ethylene glycol, diethylene glycol, propylene glycol, dipropylene glycol and tripropylene glycol, in particular the mono- and dialkyl ethers which each have at least one alkyl chain of 1 to 8 carbon atoms and/or at least one aromatic group such as, for example, propylene glycol monopropyl ether, dipropylene glycol monobutylether, tripropylene glycol monobutylether, propylene glycol dibutylether, ethylene glycol hexylether, diethylene glycol dibutyl ether, diethylene glycol phenylether, ethylene glycol phenylether, propylene glycol phenylether and dipropylene glycol phenylether.

By way of example, the ketones C6) can be aromatic, cycloaliphatic and/or aliphatic ketones having alkyl and/or aryl groups of 4 to 24 carbon atoms, such as acetophenone, benzophenone, dibutylketone, diisobutyl ketone and isobutylheptylketone.

Examples for oils and derivatives thereof C7) that are not "petroleum products" can be: a) natural oils such as oils and/or oil alkylesters of oleaginous plants such as soybean oil, rapeseed oil, rapeseed oil alkylester, corn oil, sunflower oil, cottonseed oil, linseed oil, coconut oil, coconut oil alkylester, palm oil, palm oil alkylester, safflower oil, walnut oil, peanut oil, olive oil, olive oil alkylester, castor oil and/or castor oil alkylester, the distillates thereof and/or the individual substances thereof, b) essential oils and/or individual components thereof, such as terpenes and/or terpenoids like d-limonene and/or c) synthetic oils which can be prepared according to known methods by polymerization or polycondensation of suitable compounds, their derivatives and/or their individual components, wherein the corresponding macromolecular compounds can be preserved therein, such as polyalphaolefins, polyalkylene glycols and/or polyesters. Esters in particular can be considered as derivatives.

In addition, molecular combinations of the aforementioned classes of compounds can be considered, such as intramolecularly combined ether-ester derivatives of diols and polyols C8), in particular mono-(C1-C4) alkylether monocarboxylic acid esters of diols and/or mono- or poly-alkoxylated diols, in particular acetic acid esters of mono-(C1-C4) alkyletheralkanols such as, for example, ethylene glycol monomethyl ether acetate, propylene glycol monobutylether acetate and diethylene glycol monomethylether acetate.

If the penetrant testing medium according to the invention contains less than 5 wt % of substantially water-insoluble phase C), the penetrant testing medium is not sensitive enough and the defect detection is worse. If the penetrant testing medium according to the invention, as an O/W microemulsion, contains more than 50 wt %, or as a W/O microemulsion contains more than 40 wt % of substantially water-insoluble phase C), an undesired cleavage of the microemulsion can result, an microemulsion with excess phases results, or an unstable emulsion results Moreover, it is then rather environmentally unfriendly.

The penetrant testing medium according to the invention particularly preferably contains at least one compound selected from the group of compounds comprising alcohols C2), esters and/or amides of mono-, di- and/or polycarboxylic acids C3), ethers C5) and ketones C6), or selected from the group of compounds comprising alcohols C2), esters and/or amides of mono-, di- and/or polycarboxylic acids C3) and ethers C5), or selected from the group of compounds comprising esters and/or amides of mono-, di- and/or polycarboxylic acids C3) and ethers C5). Preferably there are no further compounds of the substantially water-insoluble phase C) in the penetrant testing medium according to the invention, other than the compounds belonging to these groups.

In the microemulsions according to the invention, at least one surfactant D) is selected from among nonionic, anionic and/or amphoteric surfactants is required. Sometimes at least one surfactant acting as an emulsifier is included. The term "surfactant D)" in the context of this invention means that at least one surfactant, at least one co-surfactant and/or at least one emulsifier is/are incorporated as the surfactant D), and that at least one surfactant D) is selected from among nonionic, anionic and/or amphoteric surfactants. They particularly preferably contain at least one nonionic and at least one anionic surfactant, wherein at least one surfactant also acts as an emulsifier.

The at least one surfactant D) of the compositions of the invention can be used as an "ordinary" surfactant, as an emulsifier, as a cleaner and/or as a solvent. Emulsifiers are also surfactants and are also referred to in the context of this application as surfactants. Nonionic surfactants in particular, particularly with an HLB value approximately in the range from 8 to 20 or 9 to 18, in particular in oil/water microemulsions (O/W), or with an HLB value approximately in the range from 0 to 10, or 3 to 8, in particular in water/oil microemulsions (W/O), can act as emulsifiers. Microemulsions with surfactants having HLB values between 5 and 15 can also be used or additionally added, but cannot always be assigned specifically to these different microemulsions.

The surfactants D), and/or specific surfactants of the included surfactants D) can, for example, function as an emulsifier, as a preservative, as a solvent for at least one dye B), by way of example, as a cleaner, as a stabilizer for at least one dye B) and/or for the microemulsion, for example, as a corrosion inhibitor, to influence the viscosity of the penetrant testing medium and/or as a wetting agent to lower the surface tension for better wetting of the surface to be tested by the penetrant testing medium. In a penetrant testing medium with multiple surfactants D), each of the added surfactants D) can optionally have different abilities depending on the application.

The penetrant testing medium according to the invention contains at least 2 wt % of at least one surfactant D), preferably at least 4 wt %, or from 2 to 60 wt %, from 4 to 70 wt %, from 6 to 60 wt %, from 8 to 50 wt %, from 10 to 40 wt %, from 12 to 30 wt %, or from 14 to 25 wt %, wherein the amount range can vary significantly according to the type of microemulsion and the penetrant testing medium.

For penetrant testing media based on yellow or red fluorescent O/W microemulsions, the amount of at least one surfactant D) is preferably in the range from 2 to 60 wt %, in the range from 6 to 50 wt %, in the range from 8 to 40 wt %, or in the range from 10 to 30 wt %.

For penetrant testing media for red-white testing, based on O/W microemulsions, the amount of at least one surfactant D) is preferably in the range from 2 to 55 wt %, in the range from 8 to 45 wt %, in the range from 10 to 40 wt %, or in the range from 15 to 30 wt %.

For penetrant testing media based on yellow or red fluorescent W/O microemulsions, the amount of at least one surfactant D) is preferably in the range from 2 to 50 wt %, in the range from 10 to 40 wt %, in the range from 15 to 35 wt %, or in the range from 20 to 30 wt %.

For penetrant testing media for red-white testing, based on W/O microemulsions, the amount of at least one surfactant D) is preferably in the range from 2 to 40 wt %, in the range from 10 to 40 wt %, in the range from 15 to 35 wt %, or in the range from 20 to 30 wt %.

In principle, it is important that the penetrant testing medium according to the invention contains a surfactant D), wherein the surfactant class, and optionally also the specific surfactant compound, typically exert at least a certain influence on, in particular, viscosity and surface tension, and therefore on the quality of the penetrant testing medium. The choice of surfactant(s) D) and solvent(s) C) usually affects the operating range for the establishment and stability of a microemulsion.

In many embodiments, of the surfactants D), at least one, in particular cleaning surfactant and at least one, in particular emulsifying surfactant, or at least one, in particular cleaning surfactant, at least one, in particular microemulsion-stabilizing surfactant as a so-called co-surfactant and at least one, in particularly emulsifying surfactant, are added to the penetrant testing medium according to the invention. In this case, the surfactants and co-surfactants which are particularly used for cleaning often display exhibit more or less pronounced emulsifying action. All surfactants have a more or less pronounced cleaning effect. Many surfactants have a more or less pronounced stabilization effect on the microemulsion.

In many embodiments, at least one surfactant D) which acts primarily as an emulsifier is preferably added to the penetrant testing medium according to the invention. In many embodiments, at least one, in particular cleaning, surfactant is added to the penetrant testing medium according to the invention, which preferably enables viscosity adjustment of the penetrant testing medium for secondary tasks, such as washability from the tested surface.

In this case, the components D1 to D7 in Table 1 preferably act as emulsifiers, and the components D8 to D14 in Table 1 preferably act as co-surfactants to stabilize the microemulsion. The D16 and D17 in Table 1 preferably act as cleansing surfactant. However, these assignments depend partially upon the other surfactants which are present and the basic structure of the microemulsion, and can vary in accordance. Usually all microemulsions require at least one surfactant D) which acts as an emulsifier. The surfactants D) of the penetrant testing medium according to the invention are selected from among anionic surfactants a), nonionic surfactants b) and/or amphoteric surfactants c). The penetrant testing medium according to the invention preferably contains, as surfactant D), at least one anionic surfactant a), at least one nonionic surfactant b) and/or at least one amphoteric surfactant c).

Particularly preferred is the use of an anionic surfactant with a minimum length of the alkyl chain of 6 carbon atoms. Particularly preferred is also the use of a nonionic surfactant with a minimum length of the alkyl chain of 8 carbon atoms. For yellow and red fluorescent penetrant testing media and for penetrant testing media for red-white testing, in O/W microemulsions a content of at least one surfactant D) is preferred which has, as a non-ionic alcohol ethoxylate, an alkyl chain with 9 to 11 carbon atoms of the fatty alcohol and 5 to 10 EthO groups. For penetrant testing media as W/O microemulsions for red-white testing, a content of at least one surfactant D) is preferred which has, as the nonionic alcohol ethoxylate, an alkyl chain having 10 to 18 carbon atoms of the fatty alcohol and 2 to 10 EthO has groups.

In particular, the penetrant testing medium according to the invention can contain a combination of at least one anionic and at least one nonionic surfactant, in particular in a weight ratio of anionic to nonionic surfactants in the range from 1.0.05 to 1.10. Also particularly preferred is the combination of at least one highly water-soluble surfactant, which is soluble in water to at least 1 wt % at room temperature, with an oil-soluble surfactant.

The micelle formation of at least one surfactant D) can help in this case to increase the stability of an emulsion or microemulsion, to stabilize the single phase in an extended temperature range, and/or to make the same less sensitive to disequilibrating influences such as dilution.

Examples of anionic surfactants a) are sulfates, sulfonates, phosphates and phosphonates of hydrocarbons, carboxylic acids and/or carboxylic acid derivatives, which can optionally contain the alkylene oxide unit. The sulfates, sulfonates, phosphates, phosphonates, and carboxylic acids can be in the form of the acids or salts. Anionic surfactants of the general formula (I) are preferred:

R-Q (1).

where $Q=-O-SO_3M$, $-SO_3M$, $-O-PO_3HM$, $-PO_3HM$ or $-COOM$, wherein M is H or a cation, in particular a metal cation like an alkali metal ion, alkaline earth metal ion or an ammonium ion $R^1R^2R^3HN+$, wherein $R^1$, $R^2$ and $R^3$ are independently hydrogen and/or optionally substituting alkyl, cycloalkyl and/or aryl radicals, which can be identical or different independently of one another. Preferred radicals are, for example, hydrogen and 2-hydroxyethyl or 2-hydroxypropyl. R is preferably an unsubstituted or substituted hydrocarbon moiety having one or more alkyl chains of, in each case, 1 to 30 carbon atoms, which can optionally be bonded via alkylene oxide units; or R is preferably an alkylene oxide unit. The term 'alkylene oxide unit' particularly means units of alkylene oxides with 2 to 10 carbon atoms such as ethylene oxide, propylene oxide and/or butylene oxide, wherein the units can be arranged independently of each other within the surfactant, and accordingly randomly mixed or arranged in blocks. It is preferred that R a) is an alkyl moiety having 1 to 20 carbon atoms, such as a methyl, ethyl, propyl and/or butyl moiety, b) an aryl moiety having 6 to 24 carbon atoms such as phenyl, biphenyl and/or naphthyl, which can optionally bear one or more radicals independently of each another, such as alkyl groups each having 1 to 20 carbon atoms, such as linear or branched alkyl moieties such as secondary butyl, dodecyl or a moiety of a mono-, di- or polycarboxylic acid and/or corresponding derivatives of a) or b), such as esters or amides, for example. In this case, dicarboxylic acid esters are particularly preferred, such as succinic acid dihexylester and/or succinic acid di(2-ethylhexyl) ester, for example.

Particularly preferred anionic surfactants are alkylaryl sulfonates such as dodecylbenzene sulfonates, such as the Lutensit®-A series from BASF, alkyl sulfonates such as dodecyl sulfonates, such as the Hostapur® series from Clariant, dialkyl sulfosuccinates such as, for example, di(2-ethylhexyl)sulfosuccinates, such as the AEROSOL® series from Cytec, and/or carboxylates of carboxylic acids having 2 to 24 carbon atoms, such as sodium caprylate, potassium caprylate, sodium sebacate, potassium sebacate and ammonium isononanoate, for example. Also particularly preferred as anionic surfactants are alkyl(polyoxyethyl) phosphates such as N-alkyl(polyoxyethyl) phosphates like Phosfetal series from Zschimmer & Schwarz and/or the Rhodafac® series from Solvay (previously Rhodia), for example.

Suitable as nonionic surfactants b) are, in particular, alkoxylates such as ethoxylates, propoxylates, butoxylates and mixtures thereof, for example. The term 'alkoxylates' is used to mean compounds which contain alkylene oxide units, in particular alkylene oxide units having 2 to 10 carbon atoms, such as ethylene oxide, propylene oxide and/or butylene oxide, for example, wherein the units within the surfactant can be arranged, independently of each other, the same or differently, and particularly randomly or arranged in blocks. Examples of alkoxylates are compounds having the general formula (II):

$R^4\text{-}(AO)_w\text{—}R^5$ (11), wherein $R^4$ is preferably selected from among H, OH and alkyl groups having 1 to 30 carbon atoms, wherein $R^4$ is linear, branched or cyclic and can be saturated or unsaturated. In this case, the alkyl moiety is preferably selected from methyl, ethyl, propyl, butyl, 2-ethylhexyl, dodecyl, octadecyl, octadecenyl or aryl moieties having 6 to 24 carbon atoms, such as, in particular, phenyl or naphthyl, wherein the aryl group can optionally carry one or more moieties such as, by way of example, an arylalkyl having 1 to 30 carbon atoms, such as ethylphenyl or an alkyl with 1 to 30 carbon atoms, wherein the alkyl groups can be linear or branched, independently of one another, and are preferably 2-ethylhexyl or dodecyl. $R^4$ can be an aryloxy moiety of 6 to 24 carbon atoms, such as, in particular, phenoxy, wherein the aromatic ring can optionally carry one or more moieties such as an arylalkyl moiety having 1 to 30 carbon atoms, such as, in particular, ethylphenyl or an alkyl having 1 to 30 C atoms, where the alkyl groups can be linear or branched, independently of one another, such as in particular 2-ethylhexyl or dodecyl. Furthermore, $R^4$ can be a sorbitan ester moiety, a glycerine ester moiety, or an alkyl-$NR^6$ with an alkyl group having 1 to 30 carbon atoms, and preferably an alkyl-$NR^6$ with an alkyl group having 10 to 20 carbon atoms, wherein the alkyl group can be linear or branched and saturated or unsaturated, and can particularly be dodecyl, hexadecyl, octadecyl or octadecenyl, and wherein $R^6$ is H or an alkyl group having 1 to 20 carbon atoms, which can be linear or branched and saturated or unsaturated, and is preferably methyl, ethyl, butyl, dodecyl and/or octadecenyl. In this case, $R^5$ is preferably H or an alkyl group having 1 to 6 carbon atoms which can be linear or branched and in particular is methyl, ethyl, propyl, butyl, pentyl or hexyl.

In the general formula (II), W is a whole number in the range from 1 to 200 and AO is an alkylene oxide unit such as, in particular, $(EO)_x(PO)_y(BO)_z$. In this case, EO is an ethylene oxide unit. PO a propylene oxide unit, BO a butylene oxide, x is an integer in the range from 0 to 200, y is an integer in the range from 0 to 200 and z is an integer in the range from 0 to 200, wherein the sum of x+y+z is at least 1. The alkylene oxide unit, such as in particular $(EO)_x(PO)_y(BO)_z$ can be randomly mixed or have a block structure.

Particularly preferred nonionic surfactants b) are alcohol alkoxylates b1). These are particularly ethoxylates, propoxylates and/or butoxylates of linear or branched alcohols b1) having 1 to 30 carbon atoms, such as those of the Neodol® series from Shell. Alternatively or additionally, the preferred nonionic surfactants b) can be surfactants which are selected from among at least one of the following groups b2) to b8). Also particularly preferred are alkylene oxide block copolymers b2) such as ethylene oxide (EO)-propylene oxide (PO)-ethylene oxide (EO) block copolymers and/or butylene oxide (BO)-ethylene oxide (FO) block copolymers b3) such as the Pluronic® series from BASF. Also particularly preferred are polyalkylene oxides b4) such as, in particular, polyethylene oxides, polypropylene oxides and/or polybutylene oxides, which can be substituted on one of the two terminal oxygen atoms with hydrocarbon moieties of 1 to 24 carbon atoms, and preferably alkyl moieties of 10 to 22 carbon atoms, with linear or branched alkyl moieties of 10 to 22 carbon atoms, such as, in particular, decyl, dodecyl, tetradecyl or hexadecyl. Also particularly preferred are polyglycol ethers b5), which are particularly preferably isotridecyl-substituted, such as, for example, the Genapol® series from Clariant. Also particularly preferred are alkoxylated oils b6), such as, preferably, ethoxylated oils as in the case of many vegetable oils, such as, for example, alkoxylated and particularly ethoxylated castor oil, such as the Emulsogen® series from Clariant. Also particularly preferred are alkoxylated, for example particularly ethoxylated, fatty amines b7) having alkyl groups of particularly 10 to 22 carbon atoms, such as the Ethomeen® series from Akzo Nobel, and/or alkoxylated, in particular ethoxylated, sorbitan alkyl esters b8) with alkyl groups of, in particular, 6 to 22 carbon atoms, such as those of the AG® series from Akzo Nobel. Examples of amphoteric surfactants c) are alkyliminodipropionates such as lauryliminodipropionate, 2-ethylhexyliminodipropionate, and cocoalkyliminodipropionate, or betaines such as cocannidopropylbetaine or cocamidopropylhydroxysultaine.

Among the surfactants D), anionic surfactants a) and/or nonionic surfactants b) most of all are particularly preferred. Very particularly preferred is the incorporation of phosphoric acid monoesters and/or phosphoric acid diesters of aliphatic, cycloaliphatic and/or aromatic alcohol alkoxylates such as, by way of example, tridecanol-hexaethoxy-monophosphate, phenyl-tetraethoxy-monophosphate, di-(phenyl-tetraethoxy-)monophosphate, dodecanol-pentaethoxy-monophosphate and/or di-(dodecanol pentaethoxy-) monophosphate, and/or the incorporation of linear or branched alcohol alkoxylates b1), in particular with alcohol chain lengths in the range from 9 to 11 carbon atoms and/or with alkoxylate chain lengths in the range from 5 to 9 alkoxylate units, such as, for example, EO, and/or alkylene oxide block copolymers b2) such as ethylene oxide (EO)-propylene oxide (PO)-ethylene oxide (EO) block copolymers and/or of butylene oxide (BO)-ethylene oxide (EO) block copolymers b3).

If the penetrant testing medium according to the invention contains less than 2 wt % of at least one surfactant, there is often no microemulsion, or an unstable emulsion frequently results. If the penetrant testing medium according to the invention contains more than 30 wt %, of at least one surfactant, it usually has an environmentally unfriendly composition.

It is particularly preferred that the penetrant testing medium according to the invention contains at least one compound selected from among the group of compounds comprising anionic surfactants a) and/or nonionic surfactants b). Preferably, no further compounds of the surfactants D) are contained in the penetrant testing medium according to the invention other than the compounds among the above.

If necessary, the penetrant testing medium according to the invention can also contain at least one additive E)—in particular preservatives, corrosion inhibitors, neutralizing agents, rheological additives, hydrotropes (solubilizers), and/or cationic surfactants. The additive can particularly serve as a biocide, corrosion inhibitor, solubilizer, rheological additive and/or neutralizing agent. The additive E) can, in particular, be selected from among the group comprising preservatives such as Dantoguard® Plus Liquid from Lonza, Parmetol® MBX from Schülke, corrosion inhibitors such as octylphosphonic acid, N-oleoylsarcosine and/or Ciba® Amine O, cationic surfactants such as, by way of example, those of the general formula $R^6R^7R^8R^9N^+X^-$, and/or rheological additives such as thickeners, such as Rheovis® AT 120 from BASF, for example. The additive E) can optionally consist of multiple substances which are optionally added in the form of a solution, dispersion or paste. Water, at least one alcohol, at least one glycol, and/or at least one mineral oil typically serves as the carrier liquid. The amount of at least one additive E) is preferably in the range from 0.01 to 8 wt %, from 0.1 to 7 wt %, from 1 to 6 wt %, from 2 to 5 wt %, or from 3 to 4 wt %—or 0 wt %—wherein the content is particularly preferably 0.01 to 1 wt % of preservative and/or 0.5 to 4 wt % of corrosion inhibitor.

Suitable as cationic surfactants are, for example, quaternary ammonium compounds of the general formula $R^6R^7R^8R^9N^+X^-$, wherein the radicals $R^6$ to $R^9$ are independently selected from among linear, branched and/or cyclic, saturated or unsaturated alkyl groups having 1 to 24 carbon atoms, which are optionally substituted, and in which $X^-$ is a suitable anion such as a halide or methosulfate. Methosulfate is particularly preferred. Because they often have a halogen and/or sulfur content, cationic surfactants are less suitable, but can be advantageously used for example as biocides.

In addition, the penetrant testing medium to the invention can, if required, contain a highly water-soluble phase as a solubilizer, belonging as such to the additives E). This solubilizer can help to increase or maintain the stability of the microemulsion, in particular in the case of a dilution with water and in the event of a temperature increase and/or temperature fluctuation.

The water solubility of the solubilizer is preferably more than 10 g/L at 20° C. This category can include water-soluble alcohols having 2 to 3 carbon atoms, and/or polyols which have 2 to 5 OH groups and which independently of each other have 2 to 10 carbon atoms per alkyl group—such as glycerol, glycols, diethylene glycols and dipropylene glycols, for example. The total content of this solubilizer is preferably in the range from 0.01 to 10 wt %, or from 0.1 to 5 wt %.

Preferably the dispersion additionally contains at least one additive E) which acts as a preservative, corrosion inhibitor, neutralizing agent, solubilizer and/or rheological additive. More preferably, the penetrant testing medium according to the invention as additives E) contains only additives which act as preservatives, corrosion inhibitors, neutralizing agents, solubilizers and/or rheological additives. As shown by a number of examples of the invention, the addition of at least one solubilizer and/or a differently acting additive E) is possible but is often not necessary.

The penetrant testing medium according to the invention are preferably free from halogen-containing and/or free of sulfur-containing compounds, or have a halogen content of less than 200 ppm. If the penetrant testing media according to the invention include sulfur-containing compounds, it is preferable that the content of sulfur in the penetrant testing medium is less than 200 ppm.

Particularly preferred is a penetrant testing medium for defect detection according to the penetrant method, which contains.

A) as an O/W microemulsion, at least 30 wt %, or 30 to 85 wt %, or as a W/O microemulsion, at least 10 wt %, or 10 to 60 wt % of water A), B) at least 0.1 wt % of at least one dye B) having a solubility in water of less than 0.1 g/L at 20° C. at atmospheric pressure, which is optionally present in a dye system and which is soluble in a substantially water-insoluble liquid phase C) at a solubility of at least 10 g/L at 20° C. at atmospheric pressure.

C) at least 5 wt %, or 5 to 50 wt %, or 5 to 40 wt %, of at least one substantially water-insoluble liquid phase C) selected from the group of water-insoluble and substantially water-insoluble and organic substances which are liquid at 20° C. at atmospheric pressure, comprising hydrocarbons, including "petroleum products" C1), alcohols C2), esters of mono-, di- and/or polycarboxylic acids C3), phosphoric esters of C4), ethers C5), ketones C6), oils without "petroleum products" C7) and combined ether-ester derivatives C5), D) at least 2 wt %, or 2 to 60 wt %, or 2 to 50 wt %, of at least one surfactant D) selected from among anionic surfactants a), non-ionic surfactants b) and/or amphoteric surtactants c), and optionally E) at least one additive E), wherein the sum of all the constituents is 100 wt %, wherein the mixing ratio of water A) to surfactants D) including optionally present co-surfactants and/or emulsifiers to the substantially water-insoluble phase C) is preferably in range indicated by the corner points of 0.5:1:10, 20:1:10, 0.5:1:2 and 20:1:2 with respect to the weight ratio, and wherein the penetrant testing medium at a temperature of 20° C. at atmospheric pressure has a transparency of at least 70%, measured at 600 nm in a quartz cuvette with a thickness of the irradiated fluid of 10 mm in a Hach Lange GmbH CADA 100-V photometer, measured on a similar, but no dye-containing microemulsion and an average particle size in the range from 1 to 250 nm, measured with a Malvern Zetasizer Nano ZS with substantially single-peak particle size distributions. This determination gives an approximation of the refractive index of the water-insoluble phase C) which is taken into account in the measurement in order to obtain a more accurate measurement result.

Very preferred is a penetrant testing medium for defect detection according to the penetrant method, containing:

A) as an O/W microemulsion, at least 30 wt %, or 30 to 85 wt %, or as a W/O microemulsion, at least 10 wt %, or 10 to 60 wt % of water A), B) at least 0.1 wt % 1 wt %, of at least one dye B) having a solubility in water of less than 0.1 g/L at 20° C. at atmospheric pressure, and the optionally present in a dye system whereby as at least one dye selected from the group consisting of naphthalimides, azo dyes, anthraquinones, methine dyes and xanthenes is selected as brighteners as well as optionally at least one stilbene or at least one coumarin, C) at least 5 wt %, or 5 to 50 wt %, or 5 to 40 wt %, of at least one substantially water-insoluble liquid phase C) are independently selected from at least one substance of the carboxylic acid esters of mono-, di- and/or polycarboxylic acids, C3) and/or at least one substance of the ether C5) such as dialkyl ethers having alkyl chains each of 3 to 12 carbon atoms, D) at least 2 wt %, or 2 to 60 wt %, or 2 to 50 wt %, of at least one surfactant D), wherein at least one anionic surfactant a) with a minimum length of the alkyl chain of 6 carbon atoms, or at least one nonionic surfactant b) with a minimum length of the alkyl chain of 8 carbon atoms are included, or a combination of at least one readily water-soluble surfactant D) which is at least soluble to 1 wt % in water at room temperature with an oil-soluble surfactant D), and optionally E) at least one additive E) selected from among preservatives, corrosion inhibitors, neutralizing agents, solubilizers and rheological additives, wherein the sum of all the constituents is 100 wt %, wherein the mixing ratio of water A) to surfactants D) including optionally present co-surfactants and/or emulsifiers and to the substantially water-insoluble phase C) is preferably in the range indicated by the corner points of 0.5:1:10, 20:1:10, 0.5:1:2 and 20:1:2 with respect to the weight ratio, and wherein the penetrant testing medium at a temperature of 20° C. at atmospheric pressure has a transparency of at least 70% measured at 600 nm in a quartz cuvette with a thickness of the irradiated fluid of 10 mm as measured in a Hach Lange GmbH CADA 100-V photometer, measured on a similar, but no dye-containing microemulsion with an average particle size of at least 1 nm, measured with a Malvern Zetasizer Nano ZS.

The problem is also addressed by a method for producing a penetrant testing medium microemulsions in the form of a microemulsion, characterized in that in that first at least one dye B) or dye system is dissolved in at least one substance of the substantially water-insoluble phase C) or is dissolved in the substantially water-insoluble phase C), and in that a solution and/or a dispersion of at least one surfactant D) is then added to this solution, and subsequently water is added to this mixture (method variant 1), or in that first at least one substance of the substantially water-insoluble phase C) or the substantially water-insoluble phase C) is prepared together with at least one surfactant D) or with the surfactants D), at least one dye B) or dye system is added, and water is then added to this mixture (method variant 2), or in that water is first prepared before the other components are added (method variant 3), wherein in all method variants, only mixing and, optionally, gentle stirring, but no more energetic movements are used. In the method variant 3, to the water can be added at least one substance of the substantially water-insoluble phase C), or the substantially water-insoluble phase C), then the at least one surfactant D), the at least one dye B), or a dye system, and finally optionally at least one additive E). In all method variants, however, there is always the same microemulsion with the same characteristics.

The method variant 2 does not require the use of a second vessel for pre-dissolving the dye or the dye system, but can take longer to form a microemulsion—possibly more than 60 minutes. In all method variants, a microemulsion usually forms independently, from a thermodynamic perspective. In all method variants, it is typically sufficient of only gentle stirring is used when needed as a supportive measure.

The various components of the microemulsions according to the invention can be mixed together in different ways and in different sequences, and there is often no major differences in the mixture and in the amount of time and effort. When surfactants with a pronounced hydrophobic character are used, such as, for example, resulting from long unbranched alkyl chains such as, by way of example, in octadecenyl (hexa(oxyethyl)) phosphate or poly(oxyethyl) oleate, aggregates can form in a predominantly aqueous microemulsion due to intermolecular attraction forces, said aggregates initially causing a significant increase in the viscosity up to the formation of a gel due to the volume of surfactant in water. In this case, it is advantageous to dissolve the surfactant in the essentially water-insoluble phase C) and only then to add water A).

When anionic surfactants are used in the free acid form, it is advantageous to disperse them first in water, adjust them with an alkali or an amine to a pH in the neutral range, and to then add them to a mixture of the substantially water-insoluble phase C), dye B) and/or dye system, and optionally the additive E).

Microemulsions can be prepared in various ways. The preparation of the microemulsions can be carried out, for example, in a simple manner by mixing a water-insoluble phase C) with additional oil-soluble materials such as dye and/or additive, by heating the water-insoluble phase, and by the subsequently adding a phase containing aqueous surfactant D), and a content of water-soluble substance, while stirring. A thermodynamically stable microemulsion then typically forms spontaneously, potentially with some more stirring.

In all production variants, the preparation of the microemulsion according to the invention can be carried out in the temperature range above zero ° C. and to about 50° C., particularly at room temperature. The microemulsion can also be stored in this temperature range. It preferably has a pH ranging from 6 to 11. It is preferably used undiluted for testing.

Defects in the manufacture of the penetrant testing medium according to the invention can occur if, for example, too much mechanical force is applied with an Ultraturrax. A microemulsion will potentially not form if, in particular, the weight ratio of the substantially water-insoluble phase C) to the surfactants 1)), including optionally present co-surfactants and/or emulsifiers in an O/W microemulsion is greater than 3:1 or greater than 5:1, or if the weight ratio of water A) to surfactants D), including optionally present co-surfactants and/or emulsifiers in a W/O microemulsion is greater than 2:1 or greater than 4:1. If a temperature above 50° C. is used, a phase separation can quickly occur; however, this dispersion can often be converted into a microemulsion by stirring or shaking at a temperature below 50° C.

The microemulsions according to the present invention are preferably of the oil-in-water (O/W) type. The microemulsions then preferably contain water as the external phase, and further at least one surfactant such as, by way of example, at least one alkyl(oligo)glycoside and optionally a co-surfactant which is different from the surfactant, as well as at least one compound as the substantially water-insoluble phase C). The microemulsions can also be present as a water-in-oil emulsion (W/O), particularly if the surfactant is primarily amphoteric surfactants D and/or nonionic surfactants with a low degree of ethoxylation, for example 1-4 EthO per mole, since their spatial structure favors the formation of W/O microemulsions.

To produce a microemulsion, water A), at least one substantially water-insoluble solvent of the substantially water-insoluble liquid phase C), and at least one surfactant D) are necessary, wherein the optionally only one surfactant D), or at least one surfactant D), can also be at least one emulsifier. Then, the addition of a dye B) or dye system is still required for the microemulsion according to the invention. Once the specific concentration ranges for each component are established, the same varying individually according to the chemical system, the microemulsion usually forms automatically without the application of intensive shearing forces. A simple mixing of the components usually leads directly to formation of the optically clear or transparent microemulsion. Often the appropriate weight ratio of surfactant to water, and optionally also the appropriate weight ratio of surfactant to solvent of the substantially water-insoluble liquid phase C), is decisive to whether a so-called complete microemulsion is formed, or a microemulsion with at least one excess phase is formed. The complete microemulsion is preferred because the dye is often better distributed therein than in the microemulsion with at least one excess phase. Another factor influencing the formation of a microemulsion is possibly the temperature, because the emulsifying effect of surfactants varies according to temperature. If the temperature increases, the degree of hydration of the hydrophilic molecular constituent of the surfactant can fall. Especially in the case of non-ionic surfactants, this can lead to a reduction in the water solubility, which can be expressed by a clouding of the previously homogeneous mixture. When brought close to or beyond the clouding point, the surfactant can no longer perform its mediating function between water and oil, and breaking and/or cleaving of the microemulsion may result. Preferably, the clouding point of the added surfactants is above 50° C., above 70° C. or above 85° C. When a threshold temperature is exceeded, the microemulsion can cleave, which manifests itself by clouding and/or separation of one or more phases. The threshold temperature must be determined experimentally.

In predominantly non-aqueous W/O microemulsions, in many embodiments 10 to 60 wt % of water A), 5 to 40 wt %, of substantially water-insoluble solvent of the substantially water-insoluble phase C), and 10 to about 40 wt % of surfactant D), including optionally present co-surfactants and emulsifiers, are needed to produce a microemulsion. In predominantly aqueous O/W microemulsions, in many embodiments 30 to 85 wt % of water A), 5 to 50 wt % of substantially water-insoluble solvent of the substantially water-insoluble phase C), and 10 to about 40 wt % of surfactant D), including optionally present co-surfactants and emulsifiers, are needed to produce a microemulsion.

The microemulsion of the invention can be destabilized—by way of example chemically, if the pH changes as the result of, for example, the addition of acid, mechanically, for example by a centrifuge, by dilution, and/or by increasing the temperature, such that the water-insoluble, and substantially water-insoluble, substances separate from water. This because coalescence of the liquid droplets creates larger droplets that together continue to grow and then can form a liquid layer. This known as breaking or cleaving of an emulsion or microemulsion. If a separate layer is present, it can easily be skimmed off. Skimming can be used to further reduce the environmental risk posed by organic compounds.

The selection of at least one surfactant D) can also contribute to deciding whether to form microemulsions of the O/W or W/O type. If the HLB value of at least one surfactant D), and in particular of at least one nonionic surfactant, is in the range from about 3 to 9 or from 5 to 7, W/O microemulsions tend to form more often, while HLB values between about 8 and 20 or between 10 and 18 often lead to O/W microemulsions. In many cases, a mixture of surfactants D) is used in the penetrant testing media according to the invention, and in said mixture not all surfactants of a penetrant testing medium need to have an HLB value in this range—particularly according to the function of each individual surfactant in the penetrant testing medium. Because the HLB value is dependent on temperature, a change in temperature can also influence the micellar behavior of the surfactant. When there is a change in temperature, the interactions of a hydrophilic surfactant may decrease or increase to such an extent that an increase in temperature leads to a phase inversion of an O/W system to a W/O system, and a drop in temperature can lead to a phase inversion of a W/O system to an O/W system.

The nanodisperse structure of the microemulsion often forms with minimal stirring, while an emulsion often arises only through elaborate emulsification due to its much larger domains. Microemulsions are, as long as composition and temperature do not change, usually stable and do not display noticeable aging. Emulsions, however, are particularly sensitive to disturbance and to temperature. Heating thereof with subsequent cooling to the initial temperature leads as a rule to an irreversible change in the disperse structure, which can lead to the breaking of the emulsion as a result such that emulsion droplets flow together (coalescence) during the destabilization. It can be preferred in some embodiments that an emulsifier is added to further reduce the interfacial tension.

It has now also been found that when organic solvents with limited water-solubility are used in the substantially water-insoluble phase C), it is possible to cleave the penetrant testing medium according to the invention, the same needing to be disposed of, the contaminated remains of the penetrant testing medium according to the invention, the rinsing water and the waste water by emulsion breaking into an organic and an aqueous phase, which is advantageous for reconditioning and/or disposal of the penetrant testing medium according to the invention, and fluids which are contaminated by the same. The reconditioning and/or disposal of a penetrant testing medium, of contaminated residues of a penetrant testing medium, and/or the rinsing water and/or waste water contaminated by the same can be carried out in the presence of at least one compound of the substantially water-insoluble phase C), wherein an emulsion breaking is triggered by lowering the pH-value and/or by increasing the temperature, and wherein the liquids to be reconditioned and/or disposed are cleaved into an organic and an aqueous phase.

The present invention enables the reduction of levels of organic ingredients, particularly in organic solvents C) and/or in surfactants D), as well as the elevation of the proportion of water in the penetrant testing media, in the rinse water used in the testing and cleaning, and in liquids during the disposal of these agents, and rinse water. It allows the use of penetrant testing media which are more environmentally friendly than those of the prior art and which can be disposed of more easily and in a more environmentally friendly manner than those of the prior art. It enables the use of penetrant testing media that can be more easily removed from the test objects than the penetrant testing media of the prior art. It enables the improvement of the defect detection using a penetrant testing medium. And it also enables an improved storage stability, particularly at temperatures below 10° C.

It was surprising that it is possible, using a fairly environmentally friendly microemulsion composition, to create penetrant testing media with high or even very high detection sensitivity.

It was also surprising that penetrant testing media in the form of a microemulsion have an additional cleaning capacity, which can compensate for a potentially inadequate cleaning and/or degreasing of the parts being tested.

It was also surprising that the storage stability of the microemulsion according to the invention frequently improved, in particular at temperatures below 10° C. when dye crystallization and/or dye precipitation occurred, compared to the penetrant testing media of the prior art. It was also surprising that it is possible to produce, given a selection of a suitable solvent C) and surfactant D), fluorescent penetrant testing media with high or ultra-high sensitivity (levels 3 and 4) which also have a high water content.

The penetrant testing medium according to the invention and/or the penetrant testing medium produced according to the invention can be used particularly advantageously in fluorescent defect detection or in defect detection in the visible light range, and/or in particular defect detection of pores and/or cracks.

The penetrant testing medium according to the invention and the penetrant testing medium produced according to the invention can especially be used in automobile construction, in the aerospace industry, in plant engineering, in pipelines, in mechanical engineering, in power engineering, and in the general industry sector. In this case, it can be used advantageously in the preparation of individual components and of structures consisting of a plurality of individual components, as well as in the maintenance and the replacement of individual components and structures. They are particularly preferably used for the inspection of pipelines and pump housings in power plants.

EXAMPLES AND COMPARATIVE EXAMPLES

The examples (B) and comparative examples (VB) described below are intended to illustrate the subject matter of the invention in more detail. Aqueous compositions were prepared by mixing. Their compositions are given in Tables 2a and 2b as bath compositions.

Example 1

6 parts by weight Rhodiasolv (R) D1B—which is a mixture of diisobutyl succinate, -glutarate and -adipate—and 12.3 parts by weight Dowanol® PnB (propylene glycol n-butyl ether) were added to a beaker. With gentle stirring, 0.8 parts by weight of C1 Solvent Yellow 43 and 2.5 parts by weight of coumarin 1 (7-N,N-diethylamino-4-methyl-coumarin) were added and dissolved. To the yellow solution was added 2.5 parts by weight of propylene glycol, 5.8 parts by weight Aerosol® OT (dioctylsulfosuccinate) in the form of Aerosol® OT-85 AE containing 6.8 parts by weight of water, 7.4 parts by weight of Neodol® 91-6, and 7.4 parts by weight of Ethylan® 1003, which was then homogenized with gentle stirring. With gentle stirring, 45.3 parts by weight of demineralized water was added to the mixture, and after a few seconds of stirring, an optically clear, yellow solution was reached. The same properties of the finished microemulsions usually resulted 1) regardless of the manner of the order of addition, as indicated by process variants 1, 2 and 3, and 2) regardless of the absence of stirring or with gentle stirring, wherein the absence of stirring only leads to time delays, and gentle stirring is often necessary to save time.

In the measurement results in Table 2, there was a small number of deviations from the relationship between luminosity and defect detection level because the assignment was carried out via application-technical tests which do not include a determination of luminosity. Some of these values were higher than expected, and the dried dye films did actually have a much stronger luminosity than the standard dye film as determined visually, said standard being produced simultaneously and in the same manner as a reference for this purpose. As such, it was confirmed that penetrant testing media, which have a luminosity of greater than 110% could actually be assigned to a newer, even-higher detectability level

TABLE 1

Overview of substances added in the experiment as the components C to E

| Code | Product name | Characterization of the product | Chem Class |
|---|---|---|---|
| C1 | Rhodiasolv ® DIB | dibasic ester: mixture of diisobutylsuccinate, -glutarate, and -adipate | C3) |
| C2 | Dowanol ® PnB | propylene glycol-n-butylether | C5) |
| C3 | Rhodiasolv ® RPDE | mixture of dimethylsuccinate, -glutarate, and -adipate | C3) |
| C4 | Rhodiasolv ® IRIS | dimethyl-2-methylglutarate | C3) |
| C5 | Dowanol ® DPnB | dipropylene glycol-n-butylether | C5) |
| C6 | Dowanol ® EPh | ethylene glycol monophenylether | C5) |
| C7 | Rhodiasolv ® INFINITY | dimethyl-2-methylglutarate; contains fraction D | C3) |
| C8 | Flexisolv ® 2100C | mixture of dimethylsuccinate, -glutarate, and -adipate; contains fraction D | C3) |
| C9 | — | benzyl alcohol | C2) |
| C10 | Prifer ® 6813 | ester; composition secret | C3) |
| C11 | Dowanol ® TPnB | tripropylene glycol-n-butylether | C5) |
| C12 | — | tridecanol | C2) |
| C13 | — | diisobutylketone | C6) |
| C14 | Rhodiasolv ® ADMA | dimethyldecanamide | C3) |
| C15 | Dowanol ® PPh | propylene glycol monophenylether | C5) |
| C16 | Dowanol ® DPH 255 | mixture of ethylene glycol monophenylether and diethylene glycol monophenylether | C5) |
| D1 | Aerosol ® OT | dioctyl-sulfo-succinate | D) a) |
| D2 | Neodol ® 91-6E | $C_9$-$C_{11}$-alcohol hexaethoxylate | D) b) |
| D3 | Ethylan ® 1003 | $C_{10}$-alcohol triethoxylate | D) b) |
| D4 | Ethylan ® 1005 | $C_{10}$-alcohol pentaethoxylate | D) b) |
| D5 | Lutensol ® ON30 | short-chain fatty alcohol triethoxylate | D) b) |
| D6 | Neodol ® 91-8E | $C_9$-$C_{11}$-alcohol octaethoxylate | D) b) |
| D7 | — | sodium cumolsulfonate | D) a) |
| D8 | Sulfetal ® 4105 | sodium-2-ethylhexylsulfonate | D) a) |
| D9 | — | sodium caprylate | D) a) |
| D10 | Ampholak ® YJH-40 | sodium octyliminodipropionate | D) c) |
| D11 | Lakeland ® AMA 30 | sodium lauryliminodipropionate | D) c) |
| D12 | Triton ® H-66 | potassium fatty alcohol ester phosphate | D) a) |
| D13 | — | potassium caprylate | D) a) |
| D14 | Rhodafac ® HA-70 | polyoxyethylene phenylester phosphate | D) a) |
| D15 | Rhodafac ® RS-610E | isotridecanol hexaethoxymonophosphate | D) a) |
| D16 | Softanol ® 50 | $C_{12}$-$C_{15}$ fatty alcohol pentaethoxylate | D) b) |
| D17 | Tergitol ® 15-S-9 | $C_{12}$-$C_{15}$ fatty alcohol nonaethoxylate | D) b) |
| D18 | Mulsifan ® RT24 | fatty alcohol ethoxylate | D) b) |
| D19 | Tween ®80 | sorbitan monooleatepoly(20)ethoxylate | D) b) |
| D20 | Rhodafac ® RS-710E | isotridecanol nonaethoxymonophosphate | D) a) |
| D21 | Rhodafac ® RA-600E | polyethoxyalkyletherphosphate | D) a) |
| E1 | — | propylene glycol; solubility promoter | E |
| E2 | — | butylglycol; solubility promoter | E |
| E3 | — | sodiumhydroxide; neutralizing agent | E |
| E4 | Amine O | imidazoline derivate; corrosion inhibitor | E |
| E5 | AMP 95 | 2-amino-2-methylpropanol; corrosion inhibitor, neutralizing agent | E |
| E6 | Dantoguard ® Plus liq. | mixture of DMDM, hydantoin and iodopropynylbutylcarbamate; biocide/preservative | E |
| E7 | — | dipropylene glycol; solubility promoter | E |
| E8 | — | triethanolamine; corrosion inhibitor, neutralizing agent | E |
| E9 | Rhodafac ® ASI-80 | octylphosphonsaure; corrosion inhibitor | E |
| E10 | — | monoethanolamine; corrosion inhibitor, neutralizing agent | E |
| E11 | — | butyldiglycol; solubility promoter | E |
| E12 | Unamine O | imidazoline derivative; corrosion inhibitor | E |
| E13 | Irgamet BTZ | benzotriazole; corrosion inhibitor | E |

Examples B2 to B50 listed in Table 2b were produced and tested analogously to Example 1, wherein the at least one substance C) was the starting material, and the dye B) was added, followed by the surfactants D) and finally the additives E). This mixture was then stirred into water. Examples B51 to B62 deviated from this procedure; the at least one substance C) was the starting material, and the substances B), D), and E) were added, and then water was stirred into this mixture. For the microemulsions, this procedural difference made no difference.

TABLE 2a

Composition and properties of a penetrant testing medium in the prior art compared to a similar penetrant testing medium according to the invention

|  | Example/Comparative example | | | |
|---|---|---|---|---|
|  | CE0 | CE1 | CE2 | E0 |
| Composition in % by weight | | | | |
| A demineralized water |  | 51.6 |  | 62.3 |
| B1 Solvent Yellow 43 | 0.5 | 0.3 | 0.3 | 0.2 |
| B Lightener 1: Coumarin 1 | 0.8 | 1.1 | 1.0 | 0.5 |
| C2 Dowanol ® DPnB (dipropylene glycol-n-butylether) |  |  |  | 16.0 |
| D2 Neodol ® 91-6E | 16.7 | 17.5 |  |  |
| D6 Neodol ® 91-8E |  |  |  | 10.0 |
| D14 Rhodafac ® HA-70 |  |  |  | 4.0 |
| D16 Softanol ® 50 |  |  | 50.0 |  |
| D17 Tergitol ® 15-S-9 | 12.0 | 17.5 | 48.7 | 7.0 |
| E11 Butyldiglycol | 70.0 | 12.0 |  |  |
| Total: | 100.0 | 100.0 | 100.0 | 100.0 |
| Properties | | | | |
| Solution based on . . . * = Water-suitable solvent | * | Water and * | Surfactants |  |
| Emulsion | no | no | no | yes |
| Microemulsion | no | no | no | yes |
| Emulsion type |  |  |  | O/W |
| Stability at 50° C. | Stable | Stable | Stable | Stable |
| Stability at 0° C. | Stable | Stable | Stable | Stable |
| Average Particle size in nm | <1 | <1 | <1 | 23 |
| Transparency at 600 nm and 20° C. atm. pressure in % | 93 | 91 | 89 | 93 |
| Visually clear/transparent/milky: C. T or. M at 20° C. | C | C | C | C |
| Fault detectability class. purs. to AMS 2644 and ISO 3452 | 1 | 1 | 1 | 1 |
| luminosity of yellow fluorescent agent in % | 67 | 69 | 68 | 70 |
| For testing type red-white, yellow, red fluor.: R-W, Y, R-F | Y | Y | Y | Y |
| Cleavability in aqueous and organic phases | no | no | no | yes |

TABLE 2b

Composition and properties of penetrant testing medium; water content of the added materials is tabulated under the demineralized water A)

|  | Example/Comparative example | | | | | | | | | |
|---|---|---|---|---|---|---|---|---|---|---|
|  | E1 | E2 | E3 | E4 | E5 | E6 | E7 | E8 | E9 | E10 |
| Composition in % by weight | | | | | | | | | | |
| A demineralized water | 45.3 | 60.4 | 67.0 | 71.0 | 50.0 | 63.0 | 46.0 | 68.7 | 57.4 | 46.2 |
| B1 Solvent Yellow 43 | 0.8 |  |  |  | 2.5 | 1.0 | 1.0 | 0.3 | 0.6 | 0.8 |
| B2 Fluorescein |  | 0.4 | 1.0 | 1.0 |  |  |  |  |  |  |
| B Lightener 1: Coumarin 1 | 2.5 | 1.2 | 2.0 | 2.0 | 5.0 | 6.0 | 6.0 | 1.0 | 2.0 | 3.0 |
| C1 Rhodiasolv ® DIB (dibasic Ester) | 16.0 | 12.0 |  |  |  |  |  |  |  |  |
| C2 Dowanol ® PnB (propylene glycol-n-butylether) | 12.3 | 6.0 |  |  | 5.0 | 6.0 | 6.0 | 20.0 | 26.7 | 33.3 |
| C3 Rhodiasolv ® RPDE (dibasic Ester) |  |  | 12.0 | 12.0 | 17.5 | 16.0 | 16.0 |  |  |  |
| D1 Aerosol ® OT | 5.8 | 5.6 | 5.6 | 4.2 | 8.8 | 8.0 | 25.0 | 4.0 | 5.3 | 6.7 |
| D2 Neodol ® 91-6E | 7.4 | 6.0 | 6.0 | 4.0 | 11.2 |  |  | 6.0 | 8.0 | 10.0 |
| D3 Ethylan ® 1003 | 7.4 | 6.0 |  |  |  |  |  |  |  |  |
| D4 Ethylan ® 1005 |  |  | 4.0 | 4.0 |  |  |  |  |  |  |
| E1 propylene glycol | 2.5 | 2.4 | 2.4 | 1.8 |  |  |  |  |  |  |
| Total: | 100.0 | 100.0 | 100.0 | 100.0 | 100.0 | 100.0 | 100.0 | 100.0 | 100.0 | 100.0 |
| Properties | | | | | | | | | | |
| Emulsion | yes | yes | yes | yes | yes | yes | yes | yes | yes | yes |
| Microemulsion | yes | yes | yes | yes | yes | yes | yes | yes | yes | yes |
| Emulsion type | O/W | O/W | O/W | O/W | O/W | O/W | O/W | O/W | O/W | O/W |
| Stability at 50° C. | Stable | Stable | Stable | Stable | Stable | Unstable. Phase separation | Stable | Stable | Stable | Stable |

TABLE 2b-continued

Composition and properties of penetrant testing medium; water content of the added materials is tabulated under the demineralized water A)

| | | | | | | | | | | |
|---|---|---|---|---|---|---|---|---|---|---|
| Stability at 0° C. | Stable | Stable | Stable | Stable | Stable | Stable | Stable | Stable | Stable | Stable |
| Average Particle size in nm | 35 | 32 | 4 | 4 | 24 | 102 | 3 | 14 | 12 | 14 |
| Transparency at 600 nm and 20° C. atm. pressure in % | 91 | 92 | 89 | 87 | 91 | 72 | 90 | 92 | 93 | 92 |
| Visually clear/transparent/milky: C, T or M at 20° C. | C | C | C | C | C | T | C | C | C | C |
| Fault detectability class purs. to AMS 2644 and ISO 3452 | 3 | 0.5 | 2 | 2 | 3 | 4 | 4 | 2 | 2 | 3 |
| luminosity of yellow fluorescent agent in % | n/a | n/a | 60 | 62 | n/a | 91 | 92 | n/a | n/a | n/a |
| For testing type red-white, yellow, red fluor.: R-W, Y, R-F | Y | Y | Y | Y | Y | Y | Y | Y | Y | Y |

| | Example/Comparative example | | | | | | | | | |
|---|---|---|---|---|---|---|---|---|---|---|
| | E11 | E12 | E13 | E14 | E15 | E16 | CE17 | E18 | E19 | CE20 |
| Composition in % by weight | | | | | | | | | | |
| A demineralized water | 56.5 | 66.5 | 68.0 | 48.3 | 55.0 | 51.5 | 58.8 | 61.0 | 65.8 | 65.8 |
| B1 Solvent Yellow 43 | 0.5 | 0.5 | | | | 2.5 | | 2.0 | 0.3 | 0.3 |
| B2 Fluorescein | | | | | | | 2.0 | | | |
| B3 Neozanon ® Rot 335 (Solvent Red 122) | | | 2.0 | 2.0 | | | | | | |
| B4 Automate Red IC-HF (Solvent Red 164) | | | | | 2.0 | | | | | |
| B Lightener 1: Coumarin 1 | 1.0 | 1.0 | | | | 5.0 | 1.2 | 4.0 | 0.9 | 0.9 |
| C1 Rhodiasolv ® DIB | | | | | | | 12.0 | | | |
| C2 Dowanol ® PnB (propylene glycol-n-butyl ether) | | | | | | | 6.0 | | | |
| C3 Rhodiasolv ® RPDE | | | | | | | | 14.0 | | |
| C4 Rhodiasolv ® IRIS (dibasic Ester) | 13.0 | | | | 20.0 | 17.5 | | | | |
| C5 Dowanol ® DPnB (dipropylene glycol-n-butyl ether) | | | 20.0 | 33.0 | | 5.0 | | 4.0 | | |
| C6 Dowanol ® EPh (ethylene glycol monophenyl ether) | | 13.0 | | | | | | | | |
| C7 Rhodiasolv ® INFINITY with a high fraction of D | | | | | | | | | 33.0 | |
| C8 flexisolv ® 2100C | | | | | | | | | | 33.0 |
| D1 Aerosol ® OT | 5.0 | 4.0 | 4.0 | 6.7 | 7.0 | 3.0 | 5.6 | 6.0 | | |
| D2 Neodol ® 91-6E | 9.0 | 6.0 | 6.0 | 10.0 | 11.0 | 11.5 | 6.0 | | | |
| D3 Ethylan ® 1003 | | | | | | | 6.0 | | | |
| D4 Ethylan ® 1005 | | | | | | 4.0 | | | | |
| D5 Lutensol ® ON30 | 9.0 | 9.0 | | | | | | | | |
| D6 Neodol ® 91-8E | | | | | | | | 9.0 | | |
| E1 propylene glycol | | | | | | | 2.4 | | | |
| E1 butylglycol | 3.0 | | | | | | | | | |
| E11 butyldiglycol | 3.0 | | | | 5.0 | | | | | |
| Total: | 100.0 | 100.0 | 100.0 | 100.0 | 100.0 | 100.0 | 100.0 | 100.0 | 100.0 | 100.0 |
| Properties | | | | | | | | | | |
| Emulsion | yes | yes | yes | yes | yes | yes | yes | yes | yes | yes |
| Microemulsion | yes | yes | yes | yes | yes | yes | no | yes | yes | no |
| Emulsion type | O/W | O/W | O/W | O/W | O/W | O/W | O/W | O/W | O/W | O/W |
| Stability at 50° C. | Stable | Stable | Stable | Stable | Stable | Unstable. Phase separation | Unstable. Phase separation | Stable | Stable | Unstable. Phase separation |
| Stability at 0° C. | Stable | Stable | Stable | Stable | Stable | Stable | Unstable. Phase separation. Precipitation | Stable | Stable | Unstable. Phase separation |
| Average Particle size in nm | 7 | 23 | 4 | 3 | 3 | 12 | Not measurable | 4 | 35 | 108 |
| Transparency at 600 nm and 20° C. atm. pressure in % | 89 | 85 | 88 | 89 | 91 | 81 | 73 | 93 | 94 | 3 |
| Visually clear/transparent/milky: C, T or M at 20° C. | C | C | C | C | C | C | T | C | C | M |
| Fault detectability class purs. to AMS 2644 and ISO 3452 | 2 | 2 | 2 | 2 | 2 | 3 | 2 | 3 | 1 | 1 |
| luminosity of yellow fluorescent agent in % | n/a | n/a | n/a | n/a | n/a | n/a | n/a | n/a | n/a | n/a |
| For testing type red-white, yellow, red fluor.: R-W, Y, R-F | Y | Y | R-W | R-W | Y | Y | Y | Y | Y | Y |

TABLE 2b-continued

Composition and properties of penetrant testing medium; water content of the added materials is tabulated under the demineralized water A)

| | CE21 | E22 | E23 | CE24 | E25 | CE26 | E27 | E28 | E29 | E30 |
|---|---|---|---|---|---|---|---|---|---|---|
| Composition in % by weight | | | | | | | | | | |
| A demineralized water | 61.0 | 53.2 | 54.0 | 89.2 | 56.1 | 60.0 | 57.4 | 60.2 | 61.4 | 55.0 |
| B1 Solvent Yellow 43 | 2.0 | 1.0 | 1.0 | 0.2 | 0.9 | 1.0 | 0.9 | 0.9 | 0.9 | |
| B4 Automate Red IC-HF (Solvent Red 164) | | | | | | | | | | 7.0 |
| B Lightener 1: Coumarin 1 | 4.0 | 6.0 | 6.0 | 0.6 | 2.8 | 3.0 | 2.7 | 2.7 | 2.7 | |
| C2 Dowanol ® PnB (propylene glycol-n-butylether) | | 6.0 | 6.0 | | | | | | | |
| C3 Rhodiasolv ® RPDE | 14.0 | 16.0 | 16.0 | | | | | | | |
| C4 Rhodiasolv ® IRIS (dibasic Ester) | | | | | | | 18.0 | 14.1 | 7.2 | |
| C5 Dowanol ® DPnB (Dipropylene glycol-n- | 4.0 | | | | | | | 5.3 | | |
| C7 Rhodiasolv ® INFINITY - contains D- | | | | | 37.4 | | | | | |
| C8 Flexisolv ® 2100 C - contains D-components | | | | 10.0 | | | | | | |
| C9 benzyl alcohol | | | | | | | | 10.9 | 16.7 | 18.0 |
| D1 Aerosol ® OT | 6.0 | 6.8 | 17.0 | | | 9.8 | 7.4 | 7.6 | 7.8 | 8.4 |
| D2 Neodol ® 91-6E | 9.0 | 11.0 | | | | | | | | |
| D7 sodium-Cumolsulfonate | | | | | | | | 2.8 | 3.6 | 3.6 |
| D8 Sulfetal ® 4105 | | | | | 2.8 | 4.0 | 6.2 | 3.6 | 3.6 | 4.0 |
| E1 propylene glycol | | | | | | 4.2 | 3.2 | 3.3 | 3.3 | 3.6 |
| Total: | 100.0 | 100.0 | 100.0 | 100.0 | 100.0 | 100.0 | 100.0 | 100.0 | 100.0 | 100.0 |
| Properties | | | | | | | | | | |
| Emulsion | yes | yes | yes | yes | yes | no | yes | yes | yes | yes |
| Microemulsion | no | yes | yes | no | yes | no | yes | yes | yes | yes |
| Emulsion type | O/W | O/W | O/W | O/W | O/W | O/W | O/W | O/W | O/W | O/W |
| Stability at 50° C. | Unstable. Phase separation | Stable | Stable | Unstable. Phase separation | Stable | Unstable. Phase separation | Stable | Stable | Stable | Stable |
| Stability at 0° C. | Unstable. Phase separation | Stable | Stable | Unstable. Phase separation | Stable | Unstable. Phase separation | Unstable | Stable | Stable | Unstable. Precipitates |
| Average Particle size in nm | 610 | 87 | 24 | 420 | 32 | >1000 | 23 | 13 | 12 | 12 |
| Transparency at 600 nm and 20° C. atm. pressure in % | 1 | 89 | 90 | 2 | 91 | n/a | 95 | 94 | 94 | 86 |
| Visually clear/transparent/milky: C. T or M 20° C. | M | C | C | M | C | M | C | C | C | C |
| Fault detectability class. purs. to AMS 2644 and ISO 3452 | 4 | 4 | 4 | 1 | 3 | 3 | 3 | 3 | 3 | 2 |
| luminosity of yellow fluorescent agent in % | n/a | n/a | n/a | n/a | n/a | n/a | n/a | 89 | 88 | 87 |
| For testing type red-white, yellow, red fluor.: R-W, Y, R-F | Y | Y | Y | Y | Y | Y | Y | Y | Y | R-W |

| | E31 | E32 | E33 | E34 | E35 | CE36 | E37 | E38 | E39 | E40 |
|---|---|---|---|---|---|---|---|---|---|---|
| Composition in % by weight | | | | | | | | | | |
| A demineralized water | 51.2 | 47.0 | 49.6 | 51.0 | 51.0 | 52.0 | 49.2 | 42.7 | 31.2 | 53.2 |
| B1 Solvent Yellow 43 | | | | 0.9 | 0.9 | 0.2 | 1.0 | 0.9 | 0.2 | 0.2 |
| B4 Automate Red IC-HF (Solvent Red 164) | 6.5 | 6.5 | 6.1 | | | | | | | |
| B Lightener 1: Coumarin 1 | | | | 2.7 | 2.7 | 0.6 | 3.0 | 2.7 | 0.6 | 0.6 |
| C3 Rhodiasolv ® RPDE | | | | | | | | | | 5.6 |
| C5 Dowanol ® DPnB | | | | | | | | | 10.0 | 5.6 |
| C9 Benzyl alcohol | 18.7 | 20.5 | 17.4 | 17.8 | | | 19.6 | 18.2 | 10.0 | 7.5 |
| C10 Prifer ® 6813 | | | | | 17.8 | 19.2 | | | | |
| D1 Aerosol ® OT | 7.9 | | | | | | | | | |
| D6 Neodol ® 91-8E | 5.6 | 26.0 | 6.9 | 7.1 | 7.1 | 8.0 | 7.8 | 5.5 | 8.0 | 5.6 |
| D7 sodium-Cumolsulfonate | 3.0 | | | | | | | | | |
| D8 Sulfetal ® 4105 | 3.7 | | | | | | | | | |
| D9 sodium caprylate | | | 20.0 | 20.5 | 20.5 | | | | | 21.7 |
| D10 Ampholak ® YJH-40 | | | | | | 20.0 | | | | |
| D11 Lakeland ® AMA 30 | | | | | | | 19.4 | | | |
| D12 Triton ® H-66 | | | | | | | | 30.0 | 40.0 | |
| E1 propylene glycol | | 3.4 | | | | | | | | |
| Total: | 100.0 | 100.0 | 100.0 | 100.0 | 100.0 | 100.0 | 100.0 | 100.0 | 100.0 | 100.0 |

TABLE 2b-continued

Composition and properties of penetrant testing medium; water content of the added materials is tabulated under the demineralized water A)

Properties

| | | | | | | | | | | |
|---|---|---|---|---|---|---|---|---|---|---|
| Emulsion | yes | yes | yes | yes | yes | yes | yes | yes | yes | yes |
| Microemulsion | yes | yes | yes | yes | yes | no | yes | yes | yes | yes |
| Emulsion type | O/W | O/W | O/W | O/W | O/W | O/W | O/W | O/W | O/W | O/W |
| Stability at 50° C. | Stable | Unstable. Phase separation | Stable | Stable | Stable | Unstable. Phase separation | Stable | Stable | Stable | Stable |
| Stability at 0° C. | Stable | Stable | Stable | Stable | Stable | Unstable | Stable | Stable | Stable | Stable |
| Average Particle size in nm | 14 | 83 | 3 | 3 | 4 | 280 | 126 | 47 | 42 | 11 |
| Transparency at 600 nm and 20° C. atm. pressure in % | 90 | 86 | 90 | 90 | 91 | 2 | 79 | 80 | 82 | 95 |
| Visually clear/transparent/milky: C. T or M at 20° C. | C | C | C | C | C | M | T | C | C | C |
| Fault detectability class purs. to AMS 2644 and ISO 3452 | 2 | 2 | 2 | 3 | 3 | 1 | 3 | 3 | 1 | 1 |
| luminosity of yellow fluorescent agent in % | n/a | n/a | n/a | 88 | 89 | n/a | n/a | 89 | 54 | n/a |
| For testing type red-white, yellow, red fluor.: R-W, Y, R-F | R-W | R-W | R-W | Y | Y | Y | Y | Y | Y | Y |

| | Example/Comparative example | | | | | | | | | |
|---|---|---|---|---|---|---|---|---|---|---|
| | E41 | E42 | E43 | E44 | E45 | E46 | E47 | E48 | E49 | E50 |

Composition in % by weight

| | | | | | | | | | | |
|---|---|---|---|---|---|---|---|---|---|---|
| A demineralized water | 68.5 | 49.2 | 64.4 | 68.1 | 68.1 | 67.8 | 38.4 | 48.4 | 59.7 | 30.2 |
| B1 Solvent Yellow 43 | 0.3 | 0.5 | 0.3 | 0.3 | 0.3 | 0.3 | 0.7 | 0.7 | | |
| B Lightener 1: Coumarin 1 | 1.0 | 1.0 | 1.2 | 1.2 | 1.2 | 1.2 | 4.5 | 4.5 | | |
| B4 Automate Red IC-HF (Solvent Red 164) | | | | | | | | | | 4.8 |
| B5 Rhodamin B | | | | | | | | | 2.0 | |
| C3 Rhodiasolv ® RPDE | 7.7 | | | | | | | | | |
| C4 Rhodiasolv ® IRIS (dibasic Ester) | | | | | 5.0 | 5.0 | | | | |
| C5 Dowanol ® DPnB | 6.7 | | 19.0 | 18.0 | 13.0 | 13.0 | 19.0 | | 12.4 | 18.8 |
| C9 Benzyl alcohol | | 34.0 | | | | | | 5.0 | | |
| C11 Dowanol ® TPnB | | | | | | | | 16.0 | | |
| C12 Tridecanol | | | | | | | | | | 2.0 |
| D1 Aerosol ® OT | | 8.3 | | | | | | | | |
| D2 Neodol ® 91-6E | | | 6.0 | | 2.0 | 2.0 | 16.0 | 12.0 | | |
| D6 Neodol ® 91-8E | 4.8 | | | 4.0 | 2.0 | 2.0 | 9.0 | 7.0 | | |
| D9 sodium caprylate | 6.6 | | 8.0 | | | | | | | |
| D13 Caliumcaprylat | | | | 7.7 | 7.7 | 7.7 | | | | |
| D14 Rhodafac ® HA-70 | 2.9 | | | | | | | | | |
| D15 Rhodafac ® RS-610E | | | | | | | 5.0 | 5.0 | 4.0 | 6.0 |
| D16 Softanol ® 50 | | | | | | | | | 8.0 | |
| D17 Tergitol ® 15-S-9 | | | | | | | | | 11.0 | 22.4 |
| D18 Mulsifan ® RT24 | | | | | | | | | | 12.8 |
| E3 sodiumhydroxid | 1.1 | | | | | | | | | |
| E4 Amine O | 0.2 | | | | | 0.2 | | | | |
| E5 AMP 95 | 0.1 | | | | | | | | | |
| E6 Dantoguard ® Plus liq. | 0.1 | | | | | 0.1 | | | | |
| E7 Dipropylene glycol | | 7.0 | | | | | | | | |
| E8 Triethanolamine | | | 0.9 | 0.5 | 0.5 | 0.5 | 0.9 | 0.9 | | |
| E9 Rhodafac ® ASI-80 | | | 0.2 | 0.2 | 0.2 | 0.2 | | | 0.6 | 0.6 |
| E10 Monoethanolamine | | | | | | | 0.5 | 0.5 | 0.9 | 1.0 |
| E12 Unamine O | | | | | | | | | 0.8 | 0.8 |
| E13 Irgamet BTZ | | | | | | | | | 0.6 | 0.6 |
| Total: | 100.0 | 100.0 | 100.0 | 100.0 | 100.0 | 100.0 | 100.0 | 100.0 | 100.0 | 100.0 |

Properties

| | | | | | | | | | | |
|---|---|---|---|---|---|---|---|---|---|---|
| Emulsion | yes | yes | yes | yes | yes | yes | yes | yes | yes | yes |
| Microemulsion | yes | yes | yes | yes | yes | yes | yes | yes | yes | yes |
| Emulsion type | O/W | O/W | O/W | O/W | O/W | O/W | W/O | W/O | O/W | W/O |
| Stability at 50° C. | Stable | Stable | Stable | Stable | Stable | Stable | Stable | Stable | Stable | Stable |
| Stability at 0° C. | Stable | Stable | Stable | Stable | Stable | Stable | Stable | Stable | Stable | Stable |
| Average Particle size in nm | 37 | 62 | 11 | 10 | 10 | 10 | 45 | 74 | 5 + 32 | 6 + 44 |
| Transparency at 600 nm and 20° C. atm. pressure in % | 95 | 74 | 93 | 95 | 95 | 95 | 92 | 92 | 94 | 95 |
| Visually clear/transparent/milky: C. T or M at 20° C. | C | T | C | C | C | C | C | C | C | C |
| Fault detectability class purs. to AMS 2644 and ISO 3452 | 2 | 2 | 2 | 2 | 2 | 2 | 4 | 4 | 2 | 2 |
| luminosity of yellow fluorescent agent in % | n/a | n/a | 92 | 93 | 93 | 93 | 113* | 112* | n/a | n/a |
| For testing type red-white, yellow, red fluor.: R-W, Y, R-F | Y | Y | Y | Y | Y | Y | Y | Y | R-F | R-W |

TABLE 2b-continued

Composition and properties of penetrant testing medium; water content of the added materials is tabulated under the demineralized water A)

| | Example/Comparative example | | | | | | | | | |
|---|---|---|---|---|---|---|---|---|---|---|
| | E51 | E52 | E53 | E54 | E55 | E56 | E57 | E58 | E59 | E60 |
| Composition in % by weight | | | | | | | | | | |
| A demineralized water | 56.2 | 61.25 | 59.55 | 61.25 | 59.55 | 73.7 | 70.2 | 56.5 | 62.35 | 55.0 |
| B1 Solvent Yellow 43 | 0.2 | 0.2 | 0.2 | 0.2 | 0.2 | | | | 0.2 | |
| B Lightener 1: Coumarin 1 | 0.8 | 0.45 | 0.45 | 0.45 | 0.45 | | | | 0.45 | |
| B3 Neozapon ® Rot 335 (Solvent Red 122) | | | | | | | | 2.0 | | 2.0 |
| B5 Rhodamin B | | | | | | 2.0 | 2.0 | | | |
| C5 Dowanol ® DPnB | | 5.0 | | | | | 5.0 | | | |
| C6 Dowanol ® EPh (ethylene glycol monophenylether) | | | | | | | | 10.0 | | |
| C9 Benzyl alcohol | | | | | 2.5 | | 2.0 | | | |
| C13 Diisobutylketon | 10.0 | | | | | | | | | |
| C14 Rhodiasolv ® ADMA | | 10.0 | | | | | | 10.0 | | |
| C15 Dowanol ® PPh | | | 12.0 | 10.0 | | 6.0 | | | | |
| C16 Dowanol ® DPH 255 | | | | | 12.0 | | | | 8.0 | 14.0 |
| D2 Neodol ® 91-6E | 4.0 | | | | | 7.0 | | 10.0 | | |
| D6 Neodol ® 91-8E | 4.0 | | 10.0 | 10.0 | | | 6.0 | | 14.0 | 14.0 |
| D16 Softanol ® 50 | | | | | 10.0 | | | | | |
| D17 Tergitol 15-S-9 | | 10.0 | 10.0 | 8.0 | 10.0 | | 7.0 | | 9.0 | 9.0 |
| D19 Tween ® 80 | 15.0 | 11.0 | | | | | | 11.0 | | |
| D20 Rhodafac ® RS-710E | | | 5.0 | 4.5 | 5.0 | | 5.0 | | 3.8 | 3.8 |
| D21 Rhodafac ® RA-600E | 6.0 | | | | | 6.0 | | | | |
| E8 triethanolamine | | 1.1 | 1.1 | 1.1 | 1.1 | | 1.1 | 0.5 | 0.5 | 0.5 |
| E9 Rhodafac ASI-80 | | 0.3 | 0.3 | 0.3 | 0.3 | 0.3 | 0.3 | | 0.3 | 0.3 |
| E10 monoethanolamine | 3.8 | | 0.7 | 0.7 | 0.7 | 4.3 | 0.7 | | 0.7 | 0.7 |
| E12 Unamine O | | 0.4 | 0.4 | 0.4 | 0.4 | 0.4 | 0.4 | | 0.4 | 0.4 |
| E13 Irgamet BTZ | | 0.3 | 0.3 | 0.3 | 0.3 | 0.3 | 0.3 | | 0.3 | 0.3 |
| Total: | 100.0 | 100.0 | 100.0 | 100.0 | 100.0 | 100.0 | 100.0 | 100.0 | 100.0 | 100.0 |
| Properties | | | | | | | | | | |
| Emulsion | yes | yes | yes | yes | yes | yes | yes | yes | yes | yes |
| Microemulsion | yes | yes | yes | yes | yes | yes | yes | yes | yes | yes |
| Emulsion type | O/W | O/W | O/W | O/W | O/W | O/W | O/W | O/W | O/W | O/W |
| Stability at 50° C. | Unstable cloudiness | Stable | Stable | Stable | Stable | Stable | Stable | Stable | Stable | Stable |
| Stability at 0° C. | Stable | Stable | Stable | Stable | Stable | Stable | Stable | Stable | Stable | Stable |
| Average Particle size in nm | 3 + 12 + 580 | 35 | 7 + 64 | 5 + 49 | 6 + 39 | 8 + 57 | 65 | 43 | 5 + 36 | 6 + 38 |
| Transparency at 600 nm and 20° C. atm. pressure in % | 90 | 92 | 89 | 90 | 91 | 93 | 90 | 89 | 92 | 91 |
| Visually clear/transparent/milky: C. T or M at 20° C. | C | C | C | C | C | C | C | C | C | C |
| Fault detectability class purs. to AMS 2644 and ISO 3452 | 2 | 1 | 1 | 1 | 1 | 2 | 2 | 2 | 1 | 2 |
| luminosity of yellow fluorescent agent in % | n/a | 68 | 70 | 68 | 69 | n/a | n/a | n/a | 71 | n/a |
| For testing type red-white, yellow, red fluor.: R-W, Y, R-F | Y | Y | Y | Y | Y | R-F | R-F | R-W | Y | R-W |

| | Example/Comparative example | |
|---|---|---|
| | E61 | E62 |
| Composition in % by weight | | |
| A demineralized water | 50.8 | 60.8 |
| B3 Neozapon ® Rot 335 (Solvent Red 122) | 2.0 | |
| B5 Rhodamin B | | 2.0 |
| C6 Dowanol ® EPh (Ethylene glycol monophenylether) | 18.0 | |
| C16 Dowanol ® DPH 255 | | 8.0 |
| D6 Neodol ® 91-8E | 14.0 | 14.0 |
| D17 Tergitol 15-S-9 | 9.2 | 9.2 |
| D20 Rhodafac ® RS-710E | 3.8 | 3.8 |
| E8 Triethanolamine | 0.5 | 0.5 |
| E9 Rhodafac ASI-80 | 0.3 | 0.3 |
| E10 Monoethanolamine | 0.7 | 0.7 |
| E12 Unamine O | 0.4 | 0.4 |
| E13 Irgamet BTZ | 0.3 | 0.3 |
| Total: | 100.0 | 100.0 |

TABLE 2b-continued

Composition and properties of penetrant testing medium; water content of the added
materials is tabulated under the demineralized water A)

| Properties | | |
|---|---|---|
| Emulsion | yes | yes |
| Microemulsion | yes | yes |
| Emulsion type | O/W | O/W |
| Stability at 50° C. | Stable | Stable |
| Stability at 0° C. | Stable | Stable |
| Average Particle size in nm | 6 + 40 | 5 + 35 |
| Transparency at 600 nm and 20° C. atm. pressure in % | 89 | 91 |
| Visually clear/transparent/milky: C. T or M at 20° C. | C | C |
| Fault detectability class purs. to AMS 2644 and ISO 3452 | 2 | 2 |
| luminosity of yellow fluorescent agent in % | n/a | n/a |
| For testing type red-white, yellow, red fluor.: R-W, Y, R-F | R-W | R-F |

*For penetrant testing media B47 and B48, the microemulsions have significantly better luminosity than known in the prior art for defect detectability level 4. The knowledgeable applicant is not aware of any penetrant testing medium which has such a luminosity.

It is desirable to produce stable and as environmentally-friendly as possible microemulsions, and at the same time, either those that also meet the requirements of AMS 2644 and ISO 3452 to the greatest degree possible, and/or those which fall under a lower or higher detectability level as needed according to the product requirements and/or costs.

The success of a composition that results in a good penetrant testing medium usually cannot be determined in advance, and must be examined in each individual case since the individual components may demonstrate a generally unforeseeable interaction.

In the multiple examples, it was shown that it is possible to produce stable and largely environmentally friendly penetrant testing media in the form of microemulsions from a large variation of different raw materials from the group of dyes, solvents, surfactants and additives, wherein the penetrant testing media are advantageous over the prior art.

The AMS 2644 and ISO 3452 standards can be met in most instances Failure to meet these two standards is most likely due to an elevated halogen and/or sulfur content due to individual additives, to a slight tendency towards corrosion by individual additives, and/or to the selection of at least one nonionic surfactant having a low clouding point, such that clouding of the penetrant testing medium can easily occur when the temperature increases.

Unstable microemulsions with phase separation particularly occurred in the experiments when the weight ratio of water to the essentially water-insoluble liquid phase C) is in an unfavorable ratio for the particular surfactants used and the temperatures used. The penetrant testing medium in Example B30 is unstable at low temperature and stable at higher temperature because the dye precipitated on cooling, because the solubility limit for the dye exceeded.

The assignment of a penetrant testing medium to a detectability level is primarily dependent on the dye content and the selected dye, and to some extent on the type and amount of the at least one substance C) as a dye solvent, but is largely independent of the clarity, transparency or milkiness. However, if the content of the dye is too high, it can lead to unstable and milky systems. Since the dye content substantially influences the cost of the product, the penetrant testing media are often selected according to the need of having to use a high or low detectability level.

The visual inspection for clarity, transparency and milky appearance cannot be strictly correlated with the values of the transparency testing at 600 nm, because only a certain wavelength of light is checked.

In addition, it has been shown in the experiments that sufficient water miscibility of the substantially water-insoluble liquid phase C) with the at least one surfactant D) is particularly advantageous, which can often be seen by a transparency in the range from 70 to 100%, in the range from 70 to 80% transparency, a transition region of limited clarity occurs.

In the experiments it was found that the average particle size of the microemulsions should preferably be in the range from 1 to 130 nm, 1 to 85 or 3 to 70 nm in order to obtain and/or us stable and suitable penetrant testing media.

In further experiments, for a number of composition of high-quality examples which in Table 2b formed stable microemulsions over the entire temperature range, the dye was switched. In this case, the content of the dye was adjusted relative to the respective solubility limit and the solubility properties of this dye, and used without and with additional brighteners alternatively. There were no significant changes m this case compared to the original compositions and properties in Table 2b, such that no details are listed for these further tests. This because the average particle size and the transparency at 600 nm and 20° C. at atmospheric pressure in % changed only within a range of ±5%. The clarity and transparency as well as the suitability as a penetrant testing medium changed only slightly. The dispersions were all microemulsions. They were all stable at 0° C. and at 50° C. Only the defect detectability levels fluctuated at comparable adjusted dye content, potentially by one defect detectability level up or down, when another dye was used.

The invention claimed is:

1. A penetrant testing medium for defect detection comprising a microemulsion comprising:
   A) at least 10 wt. % water;
   B) at least 0.1 wt. % of at least one dye, wherein the dye comprises a solubility in water of less than 0.1 g/L at 20° C. and atmospheric pressure;
   C) at least 5 wt. % of at least one substantially water-insoluble liquid phase comprising one or more organic compounds, wherein the one or more organic compounds exhibit a solubility of at most 60 g/L in distilled water at 20° C. and atmospheric pressure;

D) at least 2 wt. % of at least one surfactant selected from non-ionic surfactants, anionic surfactants, amphoteric surfactants and combinations thereof;

wherein the penetrant testing medium comprises an average particle size ranging from 1 to 250 nm measured with a Malvern Zetasizer Nano ZS, and the penetrant testing medium comprises a transparency of at least 70% at 600 nm in a quartz cuvette for a 10 mm thickness of an irradiated liquid at a temperature of 20° C. and atmospheric pressure measured by a Hach Lange GmbH CADA 100-V photometer using the microemulsion absent the at least one dye.

2. The penetrant testing medium of claim 1 comprising an oil-in-water microemulsion (O/W) or water-in-oil microemulsion (W/O), wherein instead of oil, at least one other water-immiscible liquid is used.

3. The penetrant testing medium of claim 2, wherein the O/W comprises at least 30 wt. % water.

4. The penetrant testing medium of claim 2, wherein the penetrant testing medium comprises an O/W microemulsion and the penetrant testing medium further comprises:
- 30 wt. % to 80 wt. % water (A);
- 0.1 wt. % to 10 wt. % of at least one dye (B), wherein the at least one dye (B) comprises yellow fluorescent dye, red fluorescent dye, or combinations thereof;
- 5 wt. % to 50 wt. % of the at least one substantially water-insoluble liquid phase (C); and
- 2 wt. % to 60 wt. % of the at least one surfactant (D).

5. The penetrant testing medium of claim 2, wherein the penetrant testing medium comprises an O/W microemulsion and the penetrant testing medium further comprises:
- 30 wt. % to 70 wt. % water (A);
- 0.1 wt. % to 10 wt. % of at least one dye (B), wherein the at least one dye (B) comprises red dye, white dye or combinations thereof;
- 5 wt. % to 45 wt. % of the at least one substantially water-insoluble liquid phase (C); and
- 2 wt. % to 55 wt. % of the at least one surfactant (D).

6. The penetrant testing medium of claim 2, wherein the penetrant testing medium comprises an O/W microemulsion and the penetrant testing medium further comprises:
- 10 wt. % to 60 wt. % water (A);
- 0.1 wt. % to 10 wt. % of at least one dye (B), wherein the at least one dye (B) comprises yellow fluorescent dye, red fluorescent dye, or combinations thereof;
- 5 wt. % to 40 wt. % of the at least one substantially water-insoluble liquid phase (C); and
- 2 wt. % to 50 wt. % of the at least one surfactant (D).

7. The penetrant testing medium of claim 2, wherein the penetrant testing medium comprises an O/W microemulsion and the penetrant testing medium further comprises:
- 10 wt. % to 60 wt. % water (A);
- 0.1 wt. % to 10 wt. % of at least one dye (B), wherein the at least one dye (B) comprises white dye, red dye, or combinations thereof;
- 5 wt. % to 40 wt. % of the at least one substantially water-insoluble liquid phase (C); and
- 2 wt. % to 40 wt. % of the at least one surfactant (D).

8. The penetrant testing medium of claim 1, wherein the dye is selected from fluorescent dyes, dyes comprising a color in a visible light region, dyes detectable under UV light and combinations thereof.

9. The penetrant testing medium of claim 1, wherein the at least one substantially water insoluble liquid phase (C) comprises an organic solvent, the microemulsion comprises less than 40 wt. % surfactant (D) and wherein the at least one dye (B) is completely dissolved or dissolved as completely as possible in at least one compound of the substantially water-insoluble phase (C).

10. The penetrant testing medium of claim 1, wherein one or more organic compounds of the at least one substantially water insoluble liquid phase (C) are selected from alcohols, esters of carboxylic acids, amides of carboxylic acids, phosphoric esters, ethers, ketones, oils, ether derivatives of diols, ester derivatives of diols, ether derivatives of polyols, ester derivatives of polyols, and combinations thereof and derivatives thereof.

11. The penetrant testing medium of claim 1, wherein the at least one surfactant (D) also acts as an emulsifier and comprises at least one non-ionic surfactant and at least one anionic surfactant (D).

12. The penetrant testing medium of claim 1, wherein the microemulsion further comprises at least one additive (E) selected from preservatives, corrosion inhibitors, neutralizing agents, solubilizers, rheological additives and combinations thereof.

13. The penetrant testing medium of claim 1, wherein the microemulsion is single-phase, two phase or three phase.

14. The penetrant testing medium of claim 1 further comprising a luminosity of at least 60%.

15. A method for producing the penetrant testing medium of claim 1 comprising:
- dissolving the at least one dye (B) in at least a portion of the substantially water-insoluble liquid phase (C) to form a solution;
- introducing the at least one surfactant (D) into the solution to form a mixture; and
- introduction water (A) into the mixture;

wherein the at least one surfactant (D) is introduced in a solution, dispersion or combination thereof.

* * * * *